US012642553B2

(12) United States Patent
Jaeger et al.

(10) Patent No.: US 12,642,553 B2
(45) Date of Patent: Jun. 2, 2026

(54) PUNCTURE SYSTEM DELIVERY SYSTEM

(71) Applicant: RheoNexa, Inc., Deephaven, MN (US)

(72) Inventors: Jacob Jaeger, White Bear Lake, MN (US); Yves Pierre Gobin, Harrison, MN (US); Riley Vaughan, Deephaven, MN (US); Benjamin Callister, Deephaven, MN (US); Jeffrey Callister, Deephaven, MN (US); Ryan Bauer, Maple Grove, MN (US)

(73) Assignee: RheoNexa, Inc.

( * ) Notice: Subject to any disclaimer, the term of this patent is extended or adjusted under 35 U.S.C. 154(b) by 0 days.

(21) Appl. No.: 19/388,654

(22) Filed: Nov. 13, 2025

(65) Prior Publication Data

US 2026/0130689 A1 May 14, 2026

Related U.S. Application Data

(60) Provisional application No. 63/720,562, filed on Nov. 14, 2024.

(51) Int. Cl.
*A61B 17/34* (2006.01)
*A61B 17/00* (2006.01)
(Continued)

(52) U.S. Cl.
CPC .... *A61B 17/3401* (2013.01); *A61B 17/00234* (2013.01); *A61B 90/39* (2016.02); *A61M 25/0028* (2013.01); *A61M 25/003* (2013.01); *A61M 25/0108* (2013.01); *A61M 25/0662* (2013.01); *A61B 2017/00238* (2013.01);
(Continued)

(58) Field of Classification Search
CPC .......... A61B 17/3401; A61B 17/00234; A61B 2090/3966; A61M 25/0023; A61M 25/0026; A61M 25/0028; A61M 25/003; A61M 25/0108; A61M 2205/32
See application file for complete search history.

(56) References Cited

U.S. PATENT DOCUMENTS 4,552,554 A     11/1985  Gould et al.
5,135,599 A  *  8/1992   Martin .............. A61M 25/0028
                                                    604/523
(Continued)

FOREIGN PATENT DOCUMENTS

WO         2012014860        2/2012

*Primary Examiner* — Leslie R Deak
(74) *Attorney, Agent, or Firm* — MCANDREWS HELD & MALLOY, LTD

(57) ABSTRACT

A system for delivering a puncture system to puncture through a wall of a patient's blood vessel includes: a proximal catheter including a proximal lumen configured to accommodate both a primary navigation guide wire and the puncture system; a puncture system exit port in communication with the proximal lumen, wherein the puncture system exit port is configured to receive the puncture system, such that a portion of the puncture system passes through the puncture system exit port and exits the system; and a distal catheter including a distal lumen in communication with the proximal lumen, wherein the distal lumen is configured to accept the primary navigation guide wire and reject the puncture system, such that the primary navigation guide wire is able to enter the distal lumen and the puncture system is not able to enter the distal lumen.

19 Claims, 39 Drawing Sheets

(51) Int. Cl.

| | |
|---|---|
| *A61B 90/00* | (2016.01) |
| *A61M 25/00* | (2006.01) |
| *A61M 25/01* | (2006.01) |
| *A61M 25/06* | (2006.01) |

(52) U.S. Cl.

CPC .............. *A61B 2017/00309* (2013.01); *A61B 2017/00314* (2013.01); *A61B 2017/00477* (2013.01); *A61B 2017/00867* (2013.01); *A61B 2090/3966* (2016.02); *A61M 2205/0266* (2013.01); *A61M 2205/32* (2013.01); *A61M 2210/1003* (2013.01); *A61M 2210/12* (2013.01)

(56) References Cited

U.S. PATENT DOCUMENTS

| | | | | |
|---|---|---|---|---|
| 2001/0000041 | A1 | 3/2001 | Selmon et al. | |
| 2002/0065486 | A1 | 5/2002 | Balbierz et al. | |
| 2008/0154172 | A1 | 6/2008 | Mauch | |
| 2013/0245430 | A1 | 9/2013 | Selmon et al. | |
| 2013/0303897 | A1 | 11/2013 | Pursley | |
| 2020/0030588 | A1* | 1/2020 | Heilman | ............ A61M 25/0113 |
| 2020/0376239 | A1* | 12/2020 | Heilman | ............ A61M 27/006 |
| 2021/0045757 | A1 | 2/2021 | Bouasaysy et al. | |
| 2022/0160377 | A1 | 5/2022 | Rundback et al. | |

\* cited by examiner

620

650

600

650

PUNCTURE SYSTEM DELIVERY SYSTEM

CROSS REFERENCE TO RELATED APPLICATIONS

The present application claims the benefit of U.S. Prov. No. 63/720,562, filed on Nov. 14, 2024, the entirety of which is incorporated by reference herein.

BACKGROUND

Generally, this application relates to delivery systems for delivering puncture systems to puncture tissues to ultimately deliver cerebrospinal fluid (CSF) shunts. Embodiments of some such shunts are disclosed in U.S. Ser. No. 18/443,455, filed on Feb. 16, 2024, the entirety of which is incorporated by reference herein.

SUMMARY

According to embodiments, a system for delivering a puncture system to puncture through a wall of a patient's blood vessel includes: a proximal catheter including a proximal lumen configured to accommodate both a primary navigation guide wire and the puncture system; a puncture system exit port in communication with the proximal lumen, wherein the puncture system exit port is configured to receive the puncture system, such that a portion of the puncture system passes through the puncture system exit port and exits the system; and a distal catheter including a distal lumen in communication with the proximal lumen, wherein the distal lumen is configured to accept the primary navigation guide wire and reject the puncture system, such that the primary navigation guide wire is able to enter the distal lumen and the puncture system is not able to enter the distal lumen.

In an embodiment, the system further includes the puncture system, wherein the puncture system is configured to puncture through the wall of the blood vessel, interstitial tissue and dura mater into a thecal sac of the patient.

In an embodiment, the puncture system exit port is angled with respect to the center axis of the proximal lumen.

In an embodiment, a diameter of the proximal lumen is greater than a diameter of the distal lumen.

In an embodiment, a diameter of the puncture system exit port is greater than a diameter of the distal lumen.

In an embodiment, a diameter of the puncture system exit port is the same as a diameter of the proximal lumen where the puncture system exit port and the proximal lumen meet.

In an embodiment, the system further includes the puncture system, wherein the puncture system includes a stylet.

In an embodiment, the stylet is a bi-plane stylet.

In an embodiment, the stylet comprises Nitinol.

In an embodiment, the puncture system includes a catheter configured to pass over the stylet.

In an embodiment, the system further includes: a radiopaque marker on the proximal catheter; and a radiopaque marker on the distal catheter.

In an embodiment, the system further includes a connector connecting the proximal catheter and the distal catheter, wherein the puncture system exit port is in the connector.

According to embodiments, a system for delivering a puncture system to puncture through a wall of a patient's blood vessel includes: a catheter including a lumen; a puncture system exit port in the catheter and connected to the lumen, wherein the puncture system exit port opens on a sidewall of the catheter, wherein the puncture system exit port is configured to receive the puncture system, such that a portion of the puncture system passes through the puncture system exit port to exit the system; and at least one radiopaque marker configured to provide orientation information of the puncture system exit port during fluoroscopy.

In an embodiment, the system further includes the puncture system, wherein the puncture system is configured to puncture through the wall of the blood vessel, interstitial tissue and dura mater into a thecal sac of the patient.

In an embodiment: the catheter includes a proximal catheter and a distal catheter; the proximal catheter includes a proximal lumen configured to accommodate the puncture system; the distal catheter includes a distal lumen configured to accommodate a primary navigation guide wire; and the puncture system exit port is in communication with the proximal lumen.

In an embodiment, the system further includes a connector connecting the proximal catheter and the distal catheter, wherein the puncture system exit port is in the connector.

In an embodiment, the at least one radiopaque marker is located on the connector.

In an embodiment, the at least one radiopaque marker includes plurality of strips extending along an axial dimension of the system connected by a circumferential band.

In an embodiment, the plurality of strips is two strips, and wherein a first strip is longer than a second strip.

In an embodiment, the circumferential band of the radiopaque marker extends at least partially below the puncture system exit port.

Figure 1A:
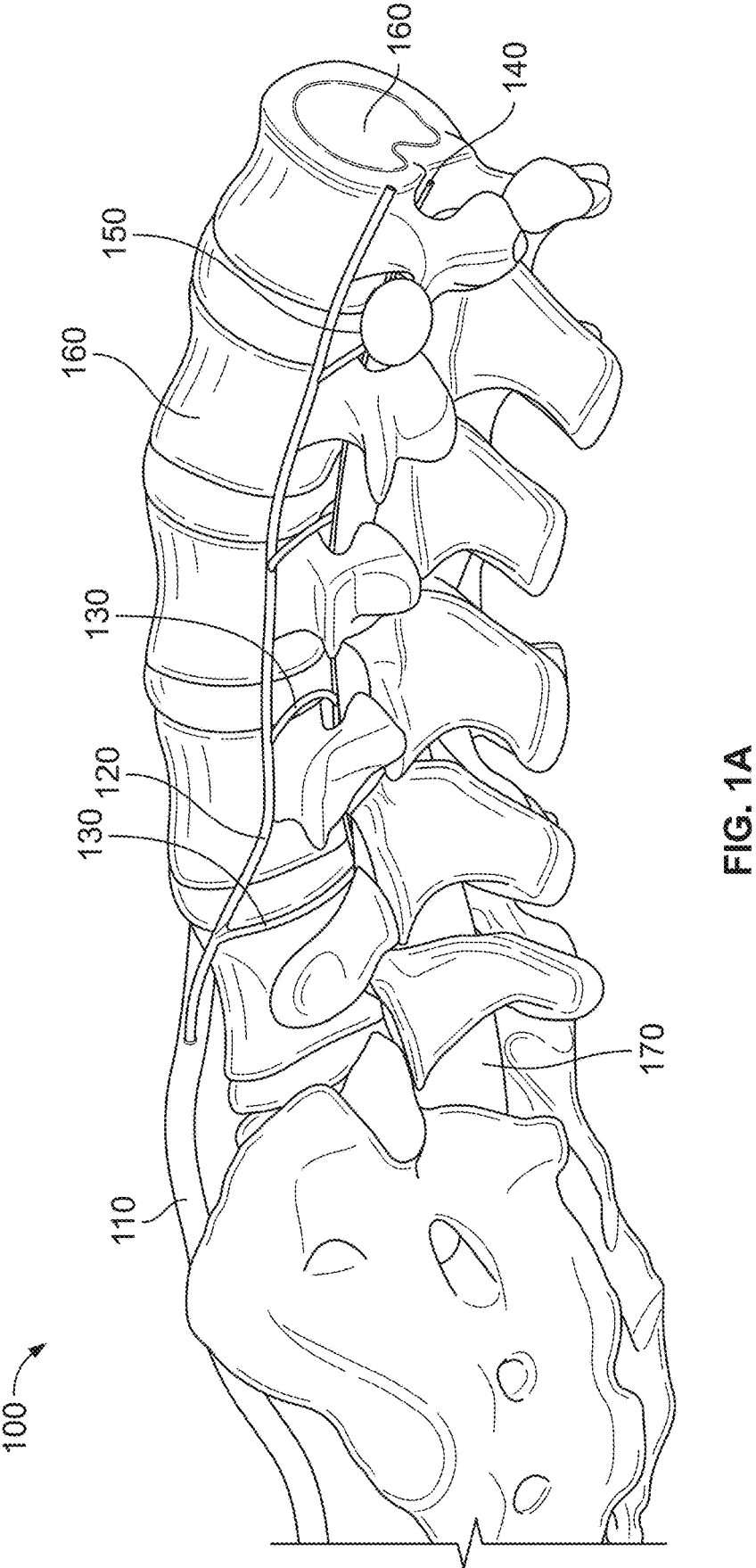
FIGS. 1A-1D illustrate patient anatomy.

The foregoing summary, as well as the following detailed description of certain techniques of the present application, will be better understood when read in conjunction with the appended drawings. For the purposes of illustration, certain techniques are shown in the drawings. It should be understood, however, that the claims are not limited to the arrangements and instrumentality shown in the attached drawings. Furthermore, the appearance shown in the drawings is one of many ornamental appearances that can be employed to achieve the stated functions of the system.

DETAILED DESCRIPTION

Figure 1B:
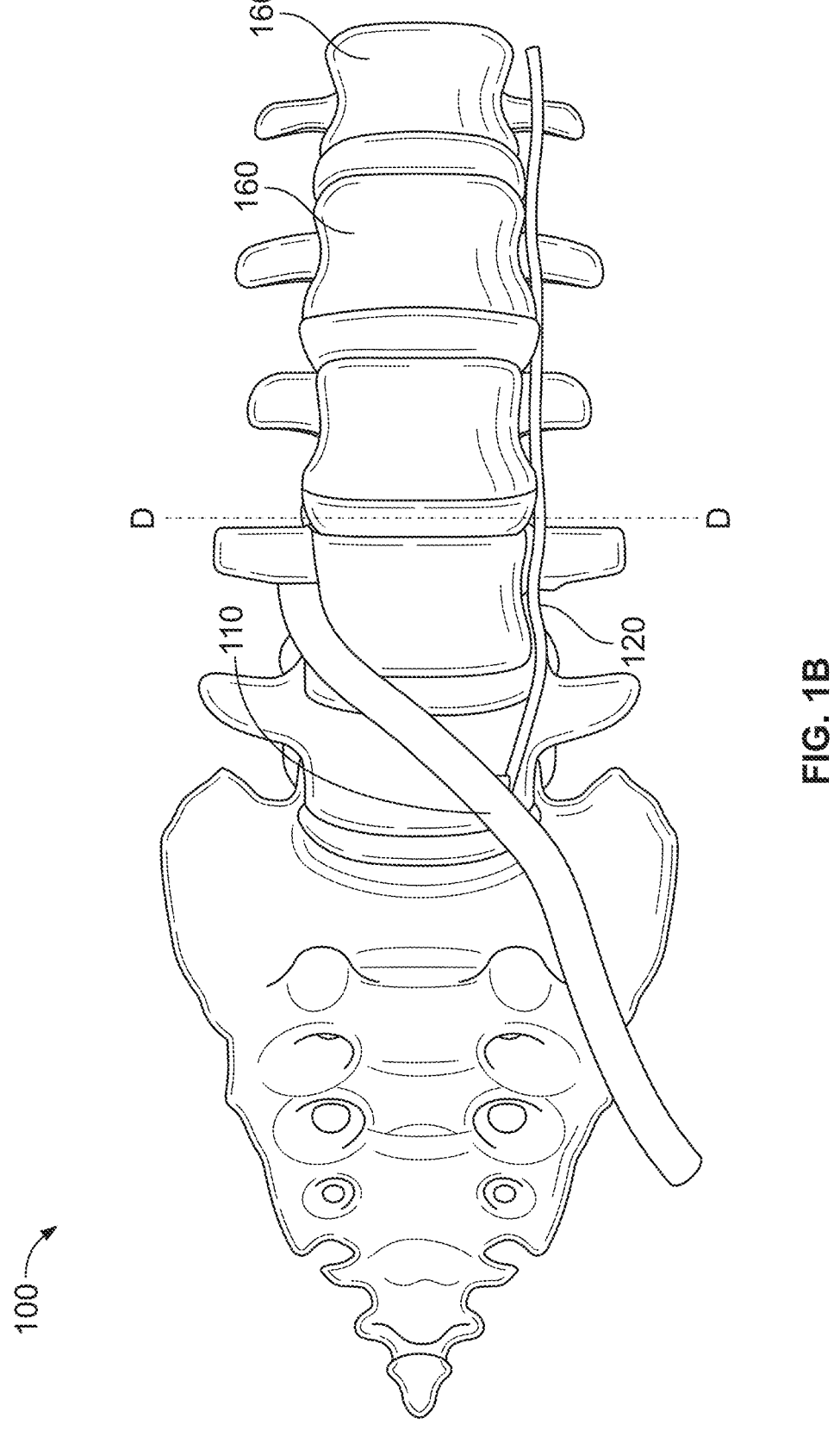
Figure 1C:
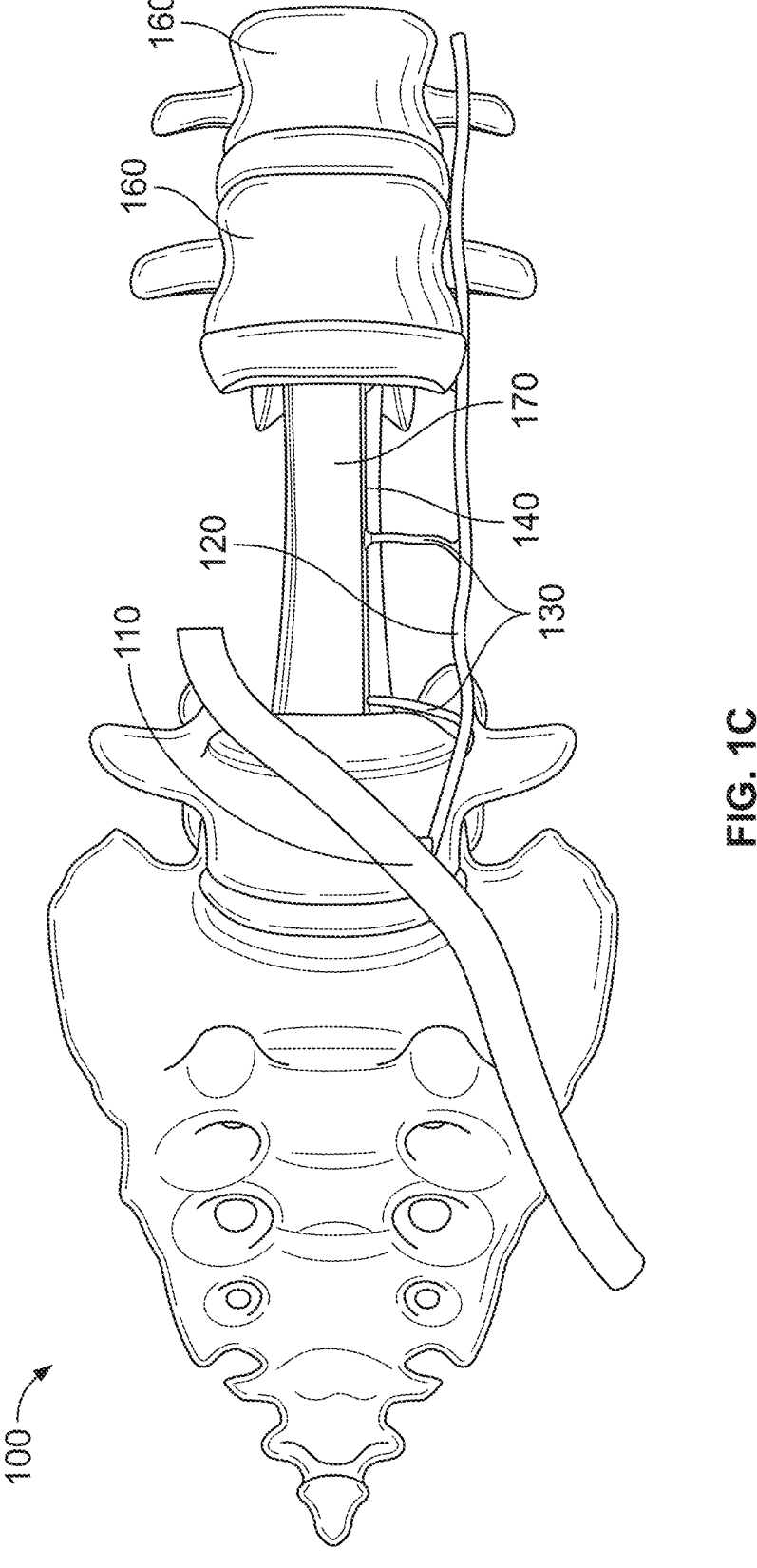
Figure 1D:
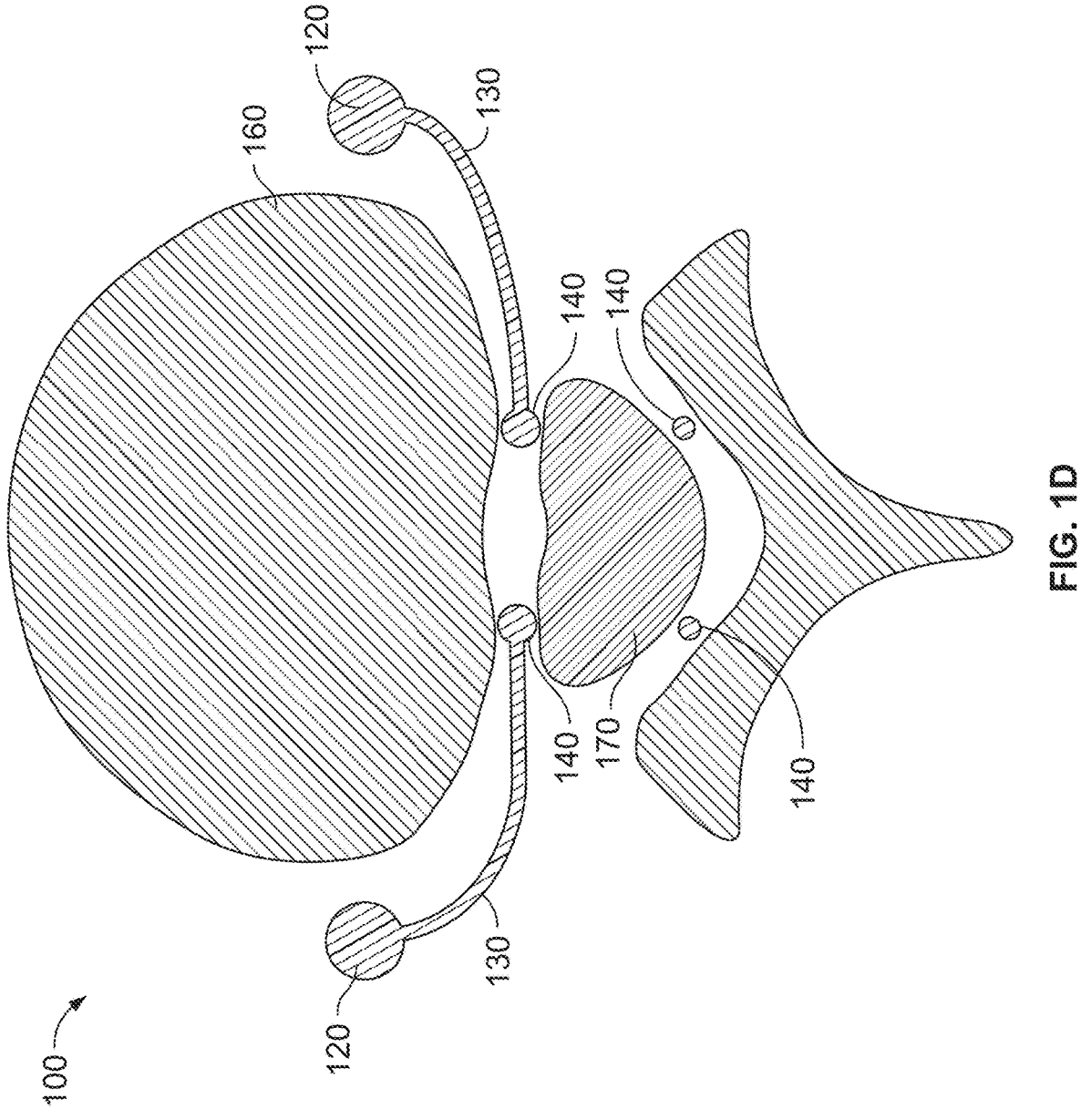

For placement and insertion of a CSF shunt system or puncture system to puncture the dura in the lumbar region of a patient's spine from a nearby vein, accurate alignment and directional orientation of a guide catheter or puncture system toward the thecal sac are essential. A portion of a patient's anatomy in the lumbar region 100 is shown in FIG. 1A (semi-lateral view), FIG. 1B (anterior view of FIG. 1A), FIG. 1C (anterior view of FIG. 1A with some of the vertebral body 160 removed), and FIG. 1D (a cross-section taken along the line D-D shown in FIG. 1B).

The intervertebral veins 130 may originate from the ascending lumbar vein 120 (which extends from the iliac vein 110) and/or the inferior vena cava. The intervertebral veins 130 take an inward (medial) sweeping path of approximately 90° around the exterior surface of the vertebral body 160, thereafter, entering the internal spinal column area through the foramen 150. Through the foramen 150, the intervertebral veins 130 join into the epidural venous plexus 140 (only left anterior side depicted in FIG. 1A). At this juncture the intervertebral veins 130 and epidural venous plexus 140 typically run between the posterior inner surface of the vertebral body 160 and the thecal sac 170. The epidural plexus 140 is composed of four longitudinal veins, two anterior and two posterior, following the antero-lateral and postero-lateral surface of the thecal sac 170. At the mid-level of the vertebral bodies 160 the two anterior venous plexus are joined by a transversal anastomosis. The venous anatomy can vary in the patient's lumbar region 100.

The shunt placement and puncture system embodiments herein (described below) may be delivered through several venous access routes including but not limited to: left or right femoral vein, left or right iliac vein 110, inferior vena cava 190, left or right ascending lumbar vein 120, left or right intervertebral veins 130, and the left or right side of both the anterior and posterior epidural venous plexus 140.

The shunt placement and puncture system may be introduced in the patient's body using suitable venous or arterial access points, such as the brachial or subclavian arteries and veins, the radial arteries, the jugular veins and carotid arteries, the femoral veins and arteries, the vena cava and abdominal aorta, and the umbilical vein and arteries of a neonate.

Figures 1E, 1F, 1G, 1H:
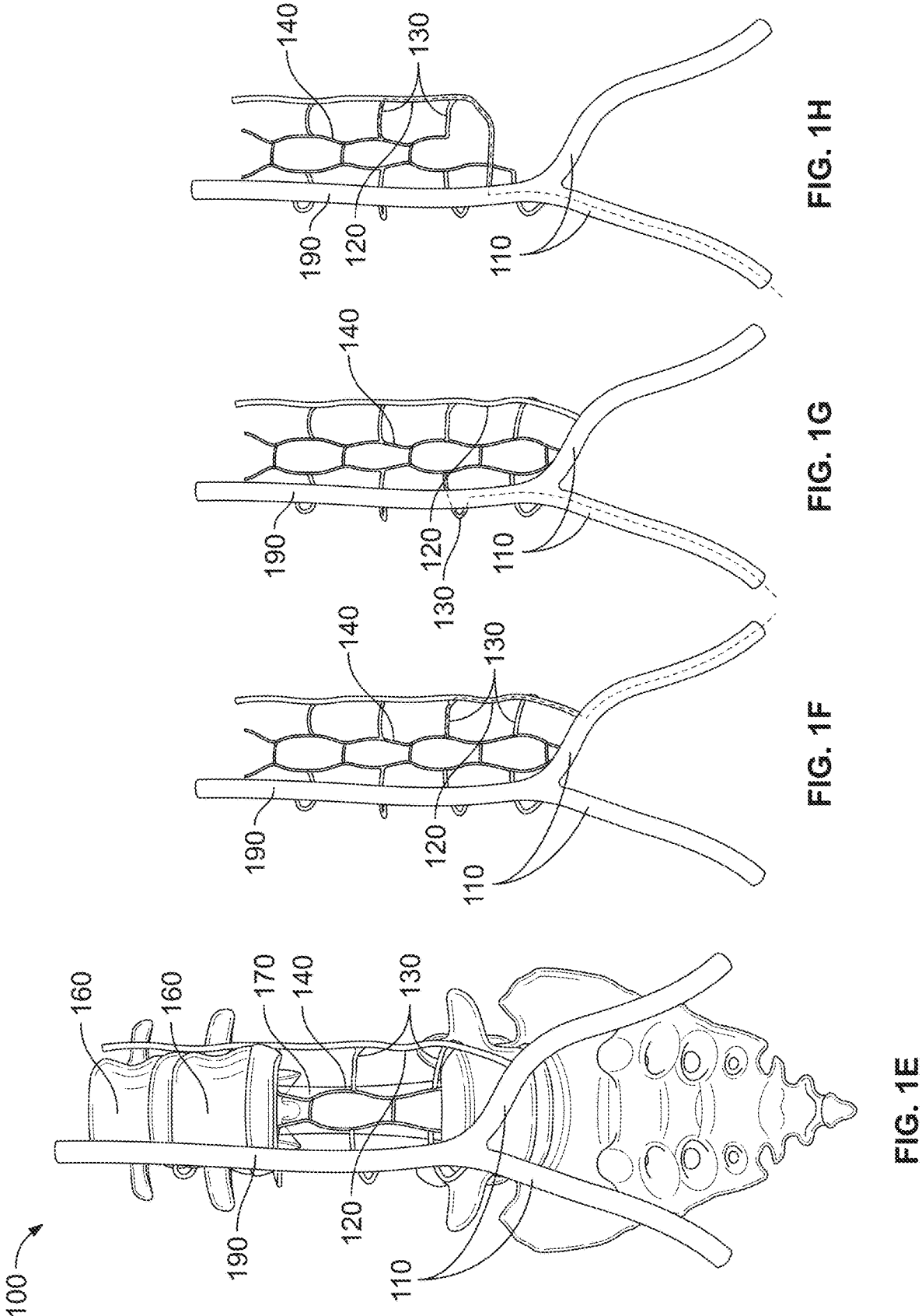
FIGS. 1E-1H illustrate different exemplary routes for implanting a CSF shunt through a patient's venous system in the lumbar region, according to embodiments.

FIGS. 1E-1H illustrate different exemplary routes for implanting a CSF shunt through a patient's venous system in the lumbar region. FIG. 1E is similar to FIG. 1C and shows more detail of the venous system. FIG. 1F shows a possible route for implanting a CSF shunt. The route is accessed through the left femoral vein, proceeds to the left iliac vein 110, then to the left ascending lumbar vein 120, and then proceeds to a left intervertebral vein 130 where the CSF shunt is situated for delivery into the thecal sac 170 (not shown in FIG. 1F). FIG. 1G shows another possible route for implanting a CSF shunt. The route is accessed through the right femoral vein, proceeds to the right iliac vein 110, and then proceeds to a right intervertebral vein 130 (via the inferior vena cava and/or the to the right ascending lumbar vein 120) where the CSF shunt is situated for delivery into the thecal sac 170 (not shown in FIG. 1G). FIG. 1H shows another possible route for implanting a CSF shunt. The route is accessed through the right femoral vein, proceeds to the right iliac vein 110, proceeds to the inferior vena cava 190, proceeds to the left ascending lumbar vein 120, and then proceeds to a left intervertebral vein 130 where the CSF shunt is situated for delivery into the thecal sac 170 (not shown in FIG. 1H).

In both anterior-posterior (AP) and lateral x-ray fluoroscopy views, the catheter system may appear perpendicular to the thecal sac 170 on a display during an implant procedure, depending on the depth of its position within the intervertebral vein 130. This can give a potentially misleading impression of the system's placement and exit orientation. Enabling accurate depth assessment and confirming positioning with multiple perspectives using techniques described herein may help to address these issues and limitations. A suitable orientation and direction of the puncture system (e.g., needle/cannula, trocar-like assembly, stylet, and/or direct shunt puncture) may be helpful for correctly puncturing the thecal sac 170 and/or direct shunt placement within the thecal sac 170.

Figure 2A:
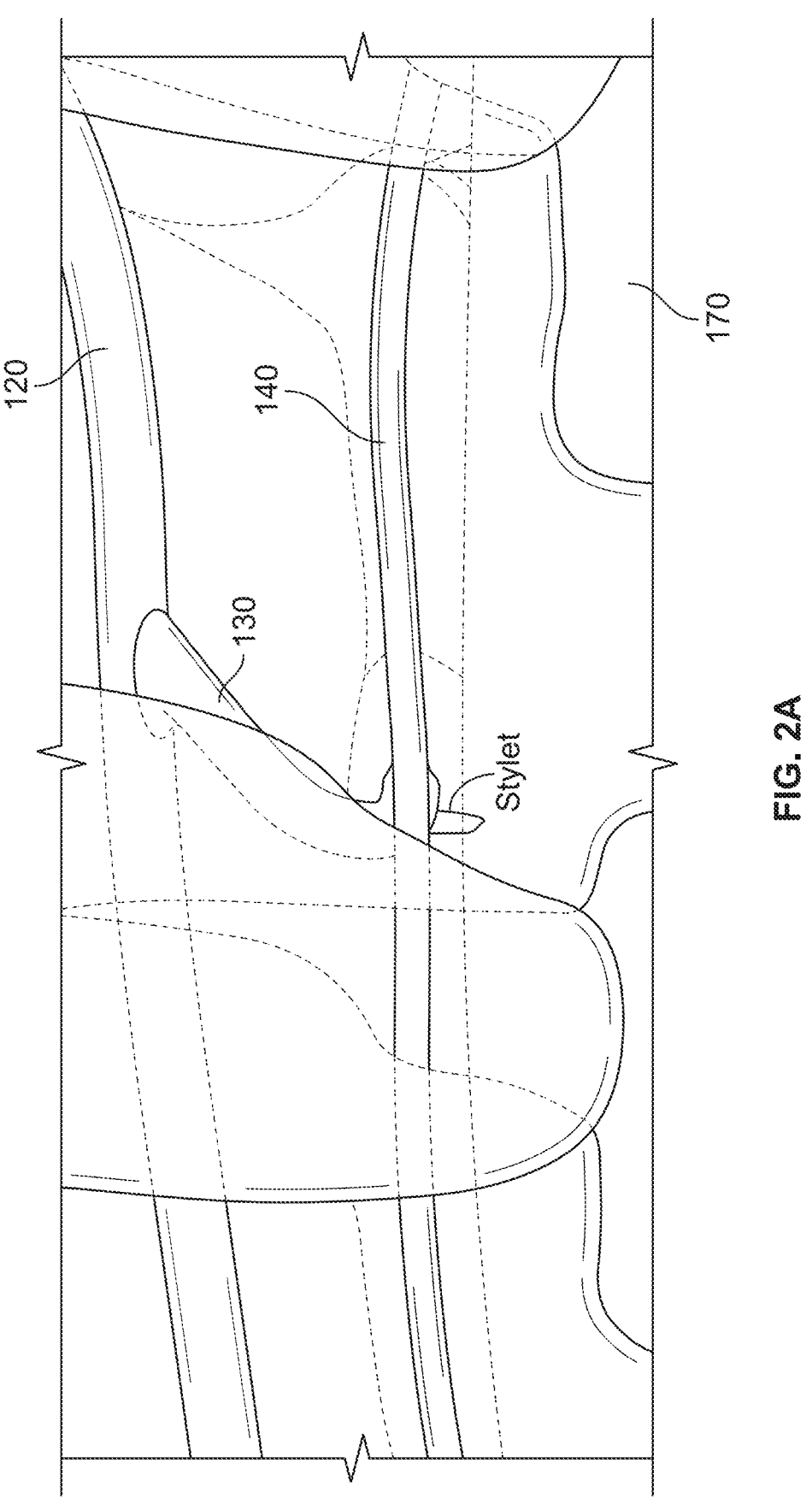
FIGS. 2A and 2B illustrate a stylet in a patient's anatomy, according to embodiments.
Figure 2B:
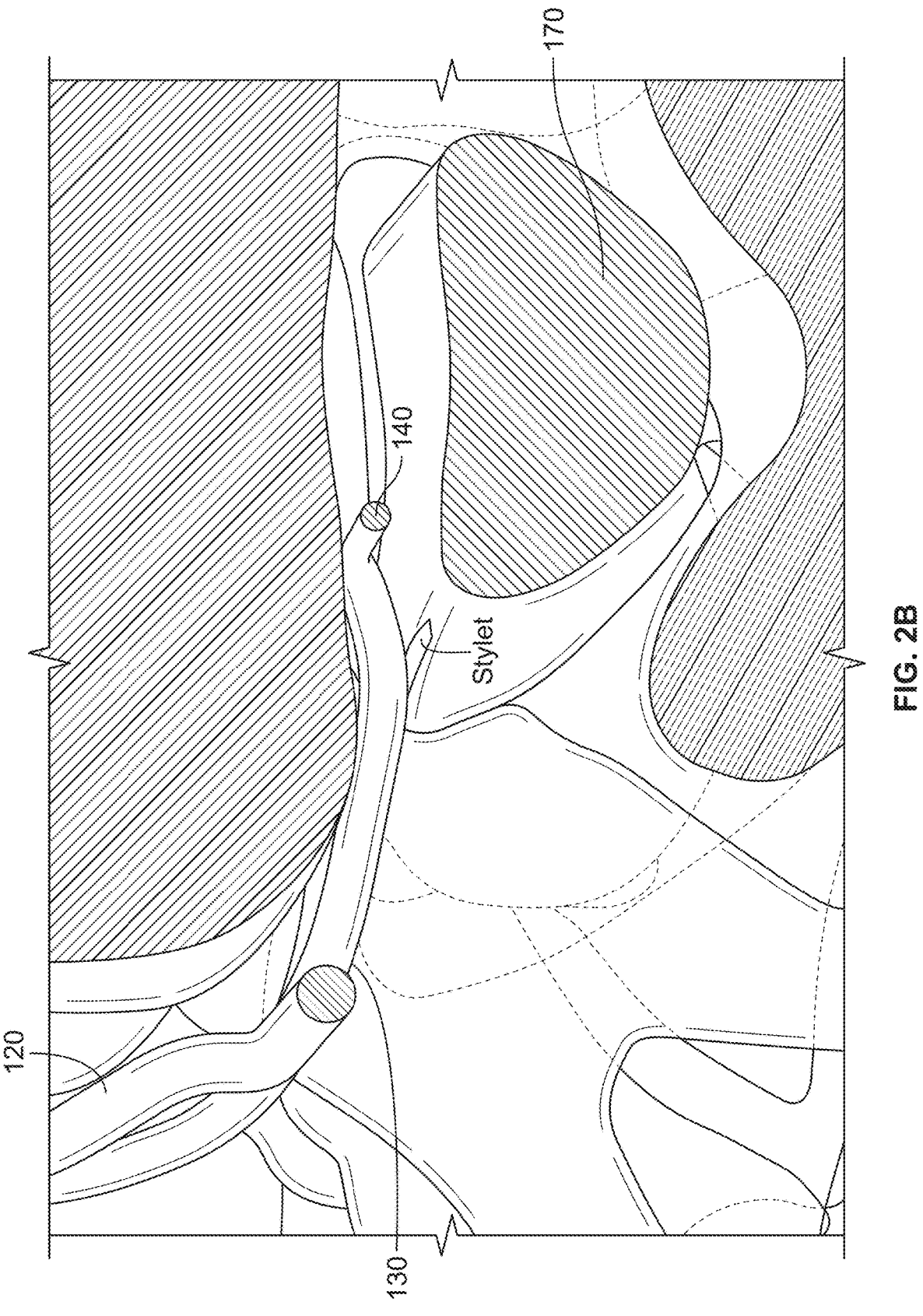

FIGS. 2A and 2B show 3D views (with FIG. 2B being a cross-sectional view) at one location in the foramen 150 illustrating how the intervertebral vein 130 branches off the lumbar vein 120 and joins into the epidural venous plexus 140. Also shown is a stylet from a puncture system (discussed further below) traversing through a vein wall proximal to the junction between the intervertebral vein 130 and the epidural venous plexus 140, and through the interstitial space and is angled posteriorly towards the thecal sac 170. The puncture system punctures interstitial tissue and dura mater for subsequent delivery and implantation of a CSF shunt.

When a puncture device or puncture system (e.g., including the depicted stylet) is moving out from the guide catheter and into the intervertebral vein (this to puncture the vein wall), it may tend to follow the vein's columnar structure during forward advancement. As can be visualized in FIG. 2A, the puncture system may exit the vein proximate the junction between the intervertebral vein 130 and the epidural venous plexus 140 and run substantially parallel to and over the thecal sac 170 in the epidural space. This may create the visual impression via fluoroscopic imaging of the puncture system (and subsequent shunt and delivery system) being at least partially within the thecal sac 170 in anterior-posterior (AP) and/or lateral views, when, in fact, the shunt or delivery system may be positioned anterior to the thecal sac 170, as the thecal sac 170 may not be visible under fluoroscopy. For at least this reason, there may be a need for a technology that orients the puncture system (and subsequent shunt delivery system) at an angle with sufficient offset from the axis of a delivery route vein in the posterior direction. In addition, it may be desirable that the puncture system, delivery system, or shunt is positioned far enough into the intervertebral vein 130 (medially) towards the thecal sac 170 to avoid nicking or puncturing the nerve root exiting the foramen 150.

Embodiments described herein may improve a physician's ability for correct shunt or delivery system placement. For example, the puncture system can be oriented to direct more posteriorly towards the thecal sac 170 and at an oblique angle to the vessel wall. The devices and features described below enable such posterior orientation from the intervertebral vein 130 and/or epidural venous plexus 140 to allow an intrathecal access by a puncture device, shunt delivery system, and/or shunt device. These features can enhance the endovascular physician's ability to orient the guide catheter and/or puncture system posteriorly, enabling improved guidance of the puncture system for a more approximately perpendicular approach and facilitating smoother, easier penetration into the thecal sac 170. The puncture system may be able to orientate between approximately 5 degrees to approximately 90 degrees from the intervertebral vein 130 axis, for example between approximately 10 and approximately 45 degrees. Depending on patient size and vessel anatomy, the systems below can range from 3 Fr upwards to 7 Fr, for example between 4.5 and 6 Fr to be able to navigate the ascending lumbar vein or intervertebral veins, for example. The delivery methods disclosed herein may describe puncturing from the anterior epidural venous plexus 140 and/or the intervertebral vein 130, but the techniques herein may be similarly applicable to the posterior epidural venous plexus 140 (or similar), and the angles would be mirrored across the frontal plane.

The techniques herein may also be applicable to different organs in different anatomies. In patients with subdural hematoma, the delivery method disclosed herein may be applied to placing a drain by puncturing a dural artery or dural vein running its course along the hematoma to drain the subdural hematoma towards the venous system or actively aspirating the hematoma if the drain has been placed through the arterial system. This technique could be extended to all types of intracranial hematoma including extradural, subarachnoid, intraventricular or parenchymatous. This technique could also be extended to puncturing the wall of an intracranial venous sinus to place a shunt into the subarachnoid space and drain cerebrospinal fluid into the intracranial venous sinus or an intracranial or extracranial vein. In patients with ascites, which is the accumulation of fluid in the peritoneal cavity, the delivery method described herein may be applied to placing a drain by puncturing a mesenteric vein or other abdominal vein to drain the ascites towards the venous system. In patients that require a neurostimulation lead or similar to be implanted in or on the surface or around the brain or a peripheral nerve, the methods of puncturing from the vein and or artery to other neural structures may be used. For example, puncturing from the sagittal sinus to access cortical or deep brain structures or puncturing through vessels in other regions of the body to access peripheral nerves in or near the neurovascular bundles. This puncture method may also be used for the placement of catheters, electrical sensing leads, electrical stimulation leads, drugs, and/or drug packages within the intrathecal space, in or around brain, or peripheral locations. The systems disclosed herein may be used for such techniques.

The tip of the guide catheter and/or puncture system may include radiopaque markers in various designs (see, e.g., FIGS. 17A-28C) to improve and to indicate the placement, direction, orientation, and/or alignment of the system's tip/puncture system exit port within the intervertebral vein 130 or epidural venous plexus 140, as will be further explained.

Figures 3A, 3B, 3C:
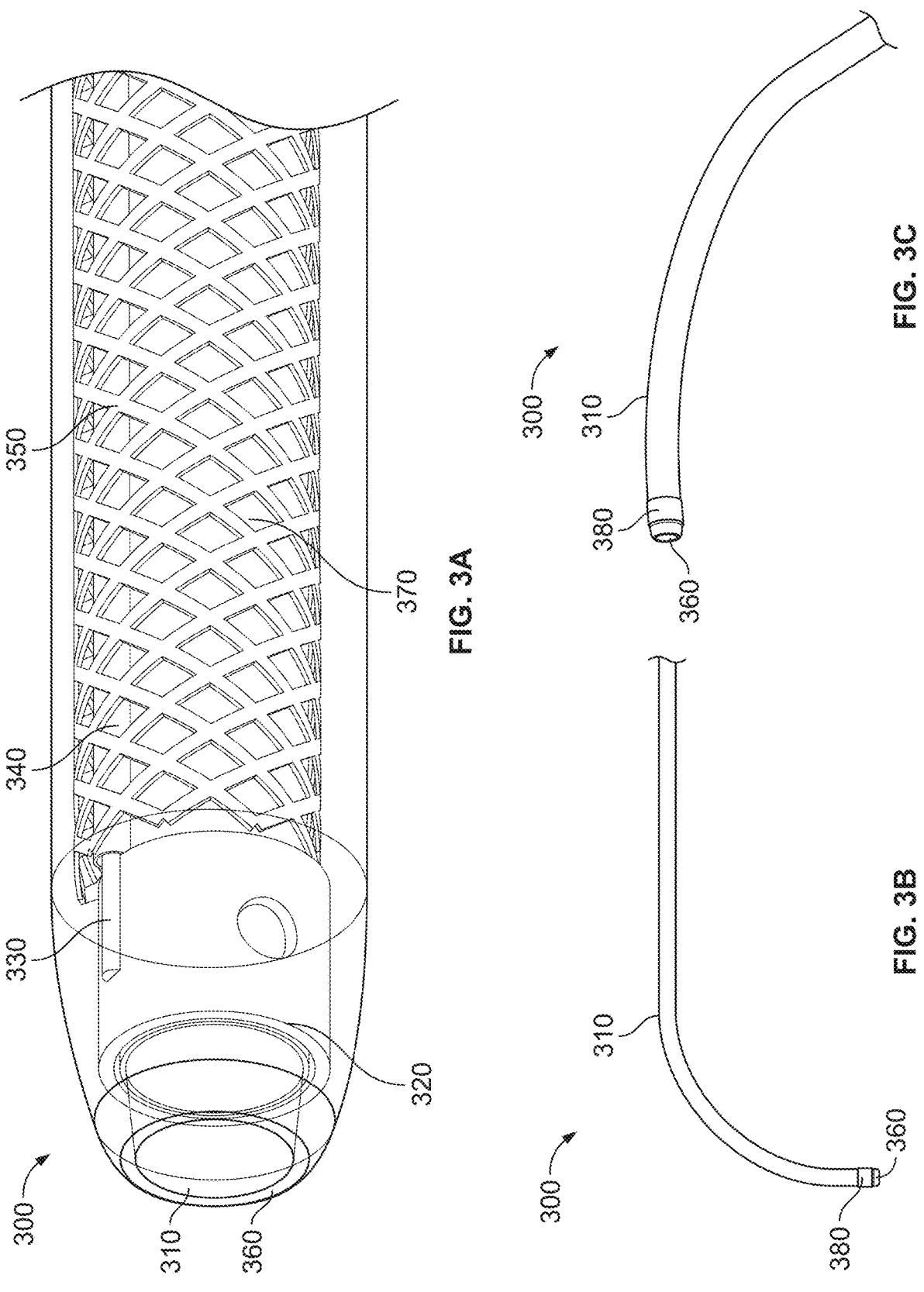
FIG. 3A illustrates a catheter with an articulated tip, according to embodiments.
FIGS. 3B-3E illustrate an articulated or bent catheter system, according to embodiments.

One exemplary technique to aid in proper placement/orientation of a distal portion of a guide catheter and/or puncture system is a component that is mechanically activated via a pull wire to angulate the tip of the component. An example of such a component is shown in FIGS. 3A-3C.

To aid in proper placement/orientation, in one example, the distal portion of a catheter 300 (e.g., guide catheter or catheter part of puncture system) can have incorporated an articulating catheter tip 360 and/or an angled tip 360 (e.g., manually activated articulating tips). This articulation or angling allows clinicians to steer and position the catheter tip 360 with improved precision during procedures, enhancing navigating the ascending lumbar vein 120, intervertebral vein 130, and the epidural venous plexus 140, and the tool to align the exit port to target the thecal sac 170 posteriorly. FIG. 3A shows an exemplary articulating system 300. FIGS. 3B and 3C illustrate the system of FIG. 3A positioned in, as an example, two angulations. FIGS. 3B and 3C further show radiopaque markers 380.

The system 300 can include a main catheter 310 (e.g., guide catheter), a pull ring 320, a pull wire 330, a pull wire tube 340, a reinforcement 350, an inner catheter 370, and/or one or more radiopaque markers 380. The pull ring 320 can be coupled with the main catheter 310, the inner catheter 370, the pull wire 330, and the reinforcement 350. The pull wire 330 can be situated within a pull wire tube 340 to retain the pull wire 330. When pulled, the pull wire 330 can pull the pull ring 320 anteriorly, thereby shortening the main catheter 310 on one side and forcing the tip 360 to bend, deflect, or otherwise articulate. Similarly, when the pull wire 330 is pushed or moved posteriorly, the pull ring 320 moves posteriorly and so does the tip 360. This lessens or removes the articulation from the system 300. A handle system, operable outside of the patient by the surgeon, can include an activation mechanism which will allow the surgeon to control the angle of articulation, and once the correct angle is achieved under fluoroscopic imaging (via the radiopaque marker(s) 380), lock the mechanism such that the angle cannot vary. An activation mechanism on the handle, as an example, can be a trigger, a turn dial, or the like, all which pull and/or push the pull wire 330 thus adjusting angulation. The handle can have a lock mechanism to lock in the desired angulation (e.g., from 5 to 90 degrees, or between 10 and 45 degrees).

Figure 3E:
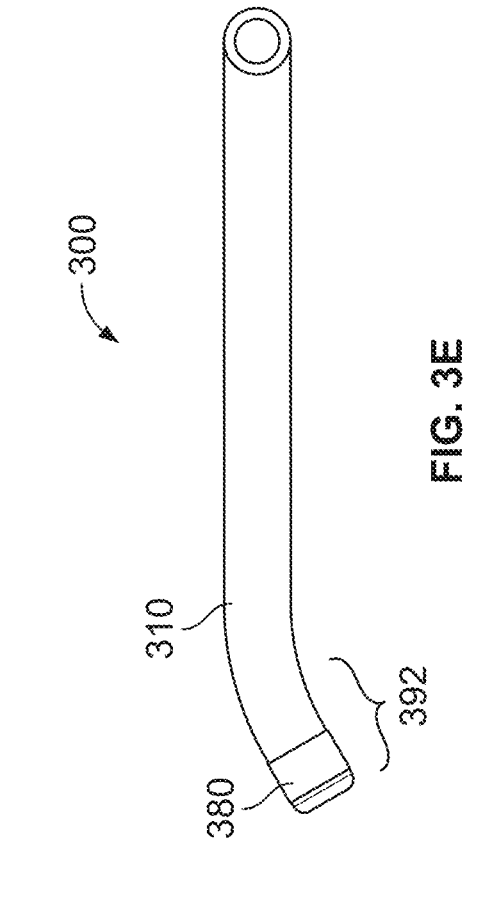
Figure 3D:
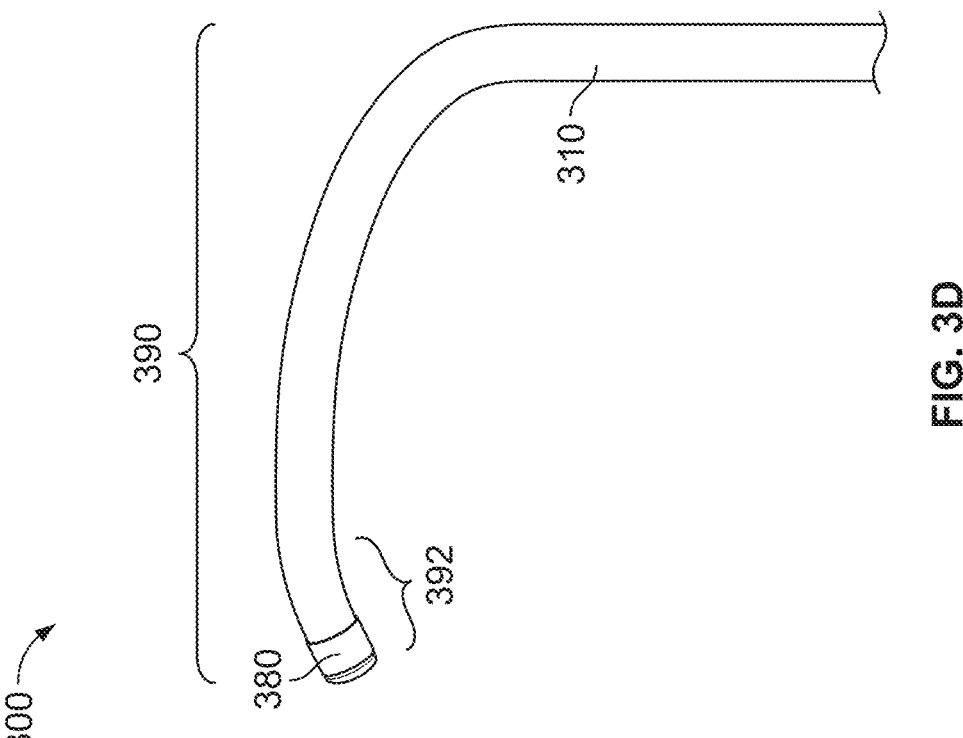

FIG. 3D shows an articulated system 300, illustrating that there may be an articulation zone 390. The articulation zone 390 may range from 5 mm to 4 cm and can have a segment 392 of the articulation zone 390 that is pre-bent (e.g., bent or deformed in advance of the procedure) and articulated out of line of the rest of the main catheter 310 as shown in FIG. 3D. FIG. 3E emphasizes that the different articulation bends could be in multiple different planes.

Figure 4A:
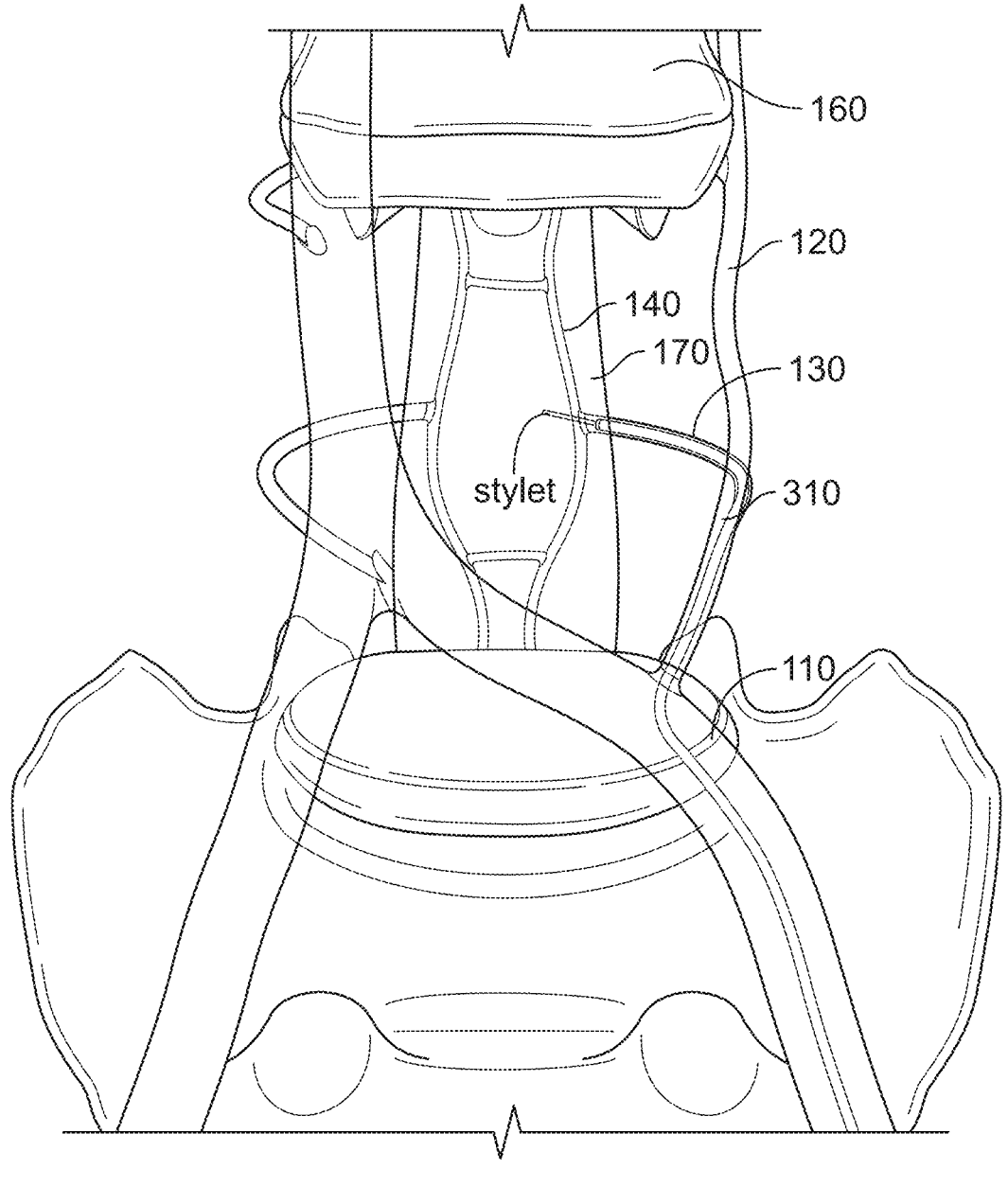
FIGS. 4A and 4B illustrate an articulating tip of a catheter with a stylet exiting into the thecal sac, according to embodiments.
Figure 4B:
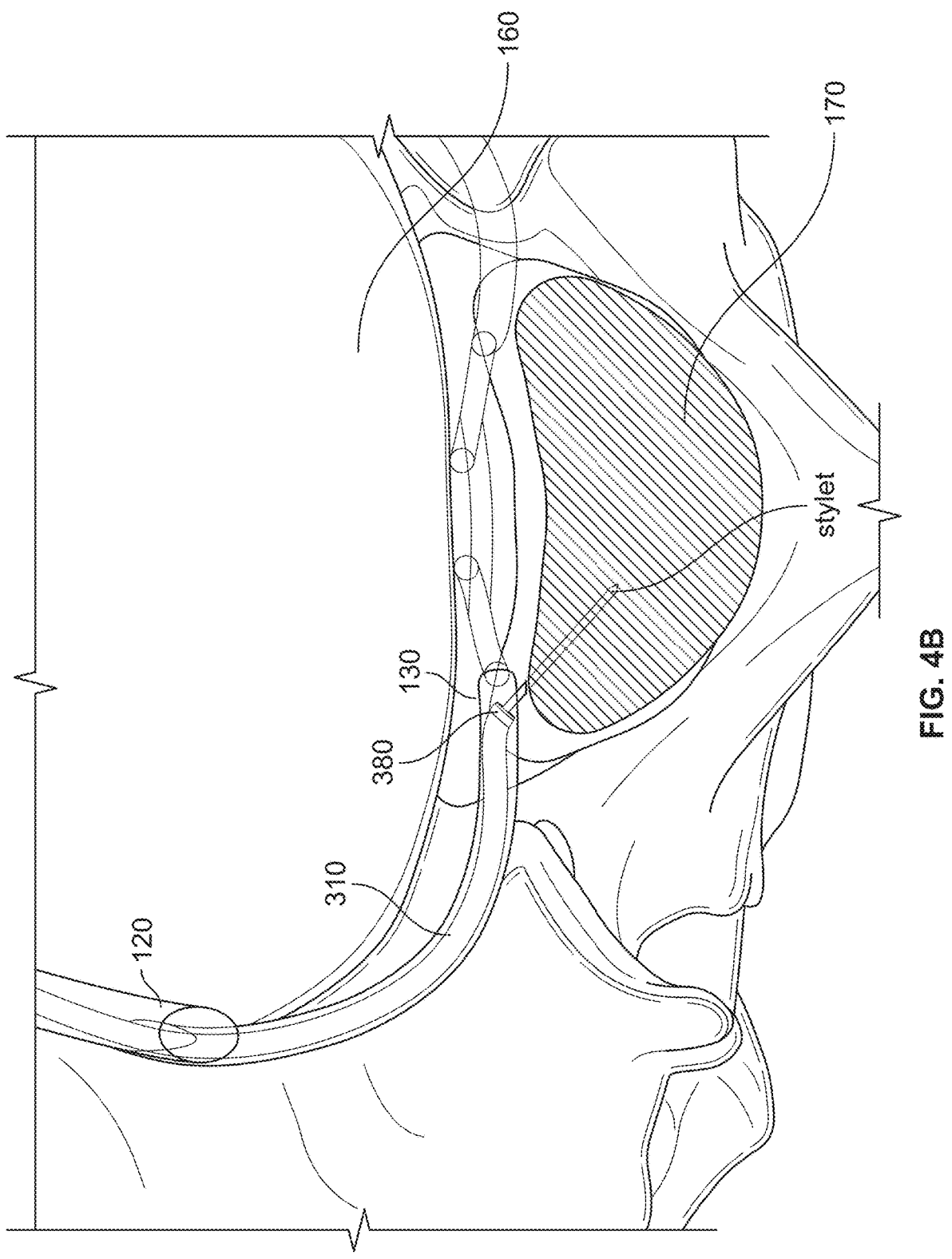

FIGS. 4A and 4B shows an example of an articulating tip of a catheter 310 (in this case, a guide catheter) with a stylet exiting posteriorly into the thecal sac 170. In this example, the access is on the left side of the patient, though it could also be accessed from the right side. The proximal articulating curve in this embodiment is set to fix/lock the catheter shaft into position in the ascending lumbar to intervertebral vein 130 curve. The distal curve is added via articulation of a pull wire 330 to increase the posterior angle of the tip 360, directing it towards the thecal sac 170. The stylet could then be advanced out of the distal end of the dual articulating tip posteriorly to puncture the thecal sac 170.

Once the tip angulation has been activated, the surgeon can lock the desired angle in place with a lock/unlock mechanism on the handle. Next the whole main catheter 310 can be rotated/torqued via the surgeon's hand which can rotate the angulated tip 360 either posterior or anterior. For left side access, a counterclockwise rotation can direct the main catheter 310 exit/tip to be orientated/angulating posteriorly towards the thecal sac 170. Once orientated and confirmed via fluoroscopic imaging and the radiopaque marker(s) 380, the surgeon can then either use a direct puncture shunt system and/or a puncturing system to gain access into the thecal sac 170. Specifically, embodiments herein for articulating and angling the distal tip 360 posteriorly (e.g., downward toward the patient's vertebral pedicles/patients back while on the operating table) can be used for consistent and appropriate puncture/placement. This additional orientation/angle can be from 5° to 90° (or from 10° to 45°) depending on the depth of the main catheter 310 in the intervertebral vein 130 and proximity to the thecal sac 170. Again, the angle can be a mirror image of itself if it traverses the right ascending lumbar vein 120 as compared to the left ascending lumbar vein 120 and into the intervertebral vein 130 and epidural venous plexus 140. The same can be said for access in the posterior epidural venous plexus 140. Thus, an angulating system 300 designed for the left ascending lumbar 120/intervertebral vein 130 showing posterior angulation, as seen from the lateral fluoroscopic display, can be anteriorly orientated if used on the right ascending lumbar vein 120/intervertebral vein 130.

The embodiments herein are not limited to the specific anatomies described and depicted but rather can be applicable different areas of the spinal system, as will be understood, taking different paths along the different vessel architecture to gain access into the foramen 150.

Figures 5A, 5B:
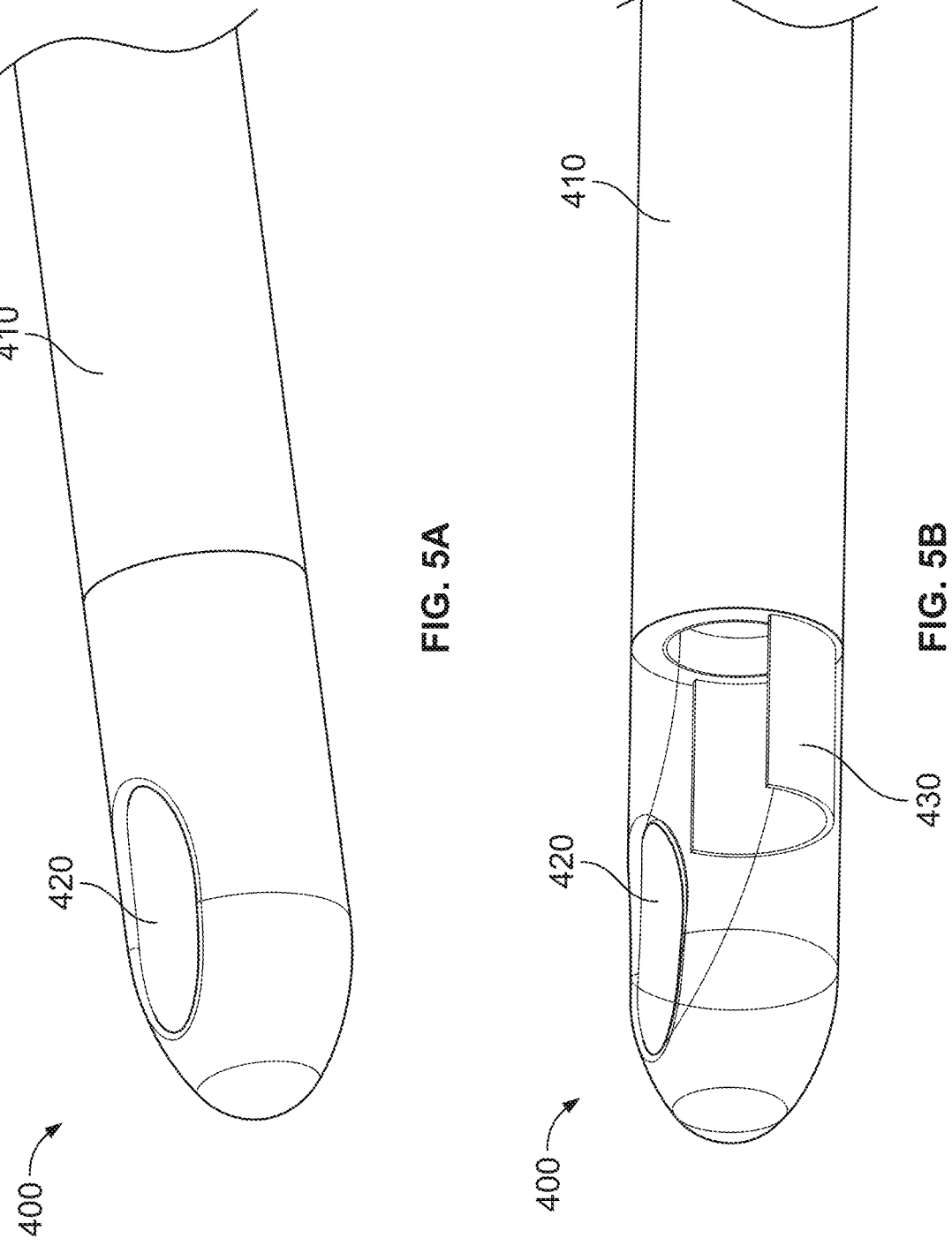
FIGS. 5A-5C illustrate a puncture system delivery system in which a catheter has a puncture system side exit port at a distal region, according to embodiments.
Figure 5C:
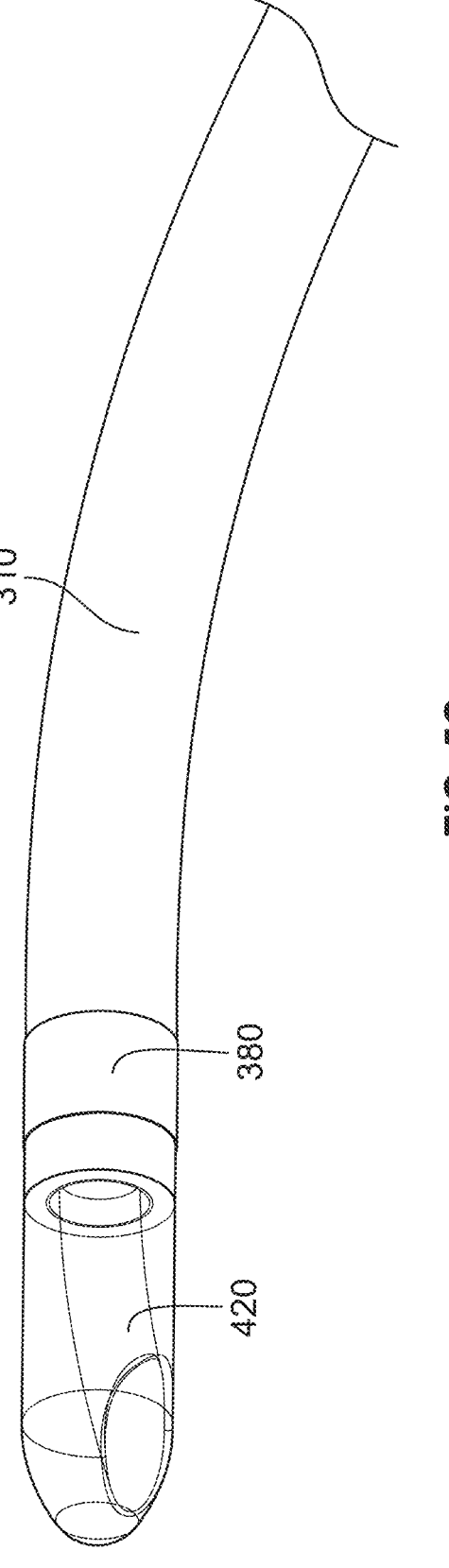

FIGS. 5A-5C show a system 400 in which the catheter 410 has a puncture system exit port 420 at the distal region. The puncture system exit port 420 may be continuous with the inner passage of a catheter 410. The puncture system exit port 420 may be angled from the center axis from the lumen from which it extends in the catheter 410. The puncture system exit port 420 extends along this angle to an exit aperture. The puncture system exit port 420 may open on a sidewall of the catheter 410, instead of at the distal tip. The puncture system exit port 420 may have a center axis with a curved radius, such that it has a scoop shape. A puncture system (not shown in FIGS. 5A-5C) can be delivered through the lumen in the catheter 410 through the puncture system exit port 420, when it is deployed to puncture a patient's dura to implant a CSF shunt in the patient's thecal sac 170. The system 400 in FIG. 5A shows a solid view and FIG. 5B shows a transparent view, and further shows a radiopaque marker 430 (in this example, a half-ring) embedded in the tip and underneath the region leading up to and a portion of the puncture system exit port 420. FIG. 5C shows another example of a puncture system exit port 420, which is used in conjunction with the articulation system 300 depicted in FIGS. 3A-3E. When the distal tip of the system is positioned with its exit oriented posteriorly within the distal segment of the intervertebral vein 130 and/or epidural venous plexus 140, and confirmed in both lateral and antero-posterior fluoroscopy through particular radiopaque marker(s) 380 placements and structures, advancing the system 400 forward with respect to the puncture system exit port 420 can direct the distal tip posteriorly. This orientation can enable improved puncturing of the vessel wall, interstitial space, and dura, allowing direct access into the thecal sac 170 for the puncture system.

Figures 6A, 6B:
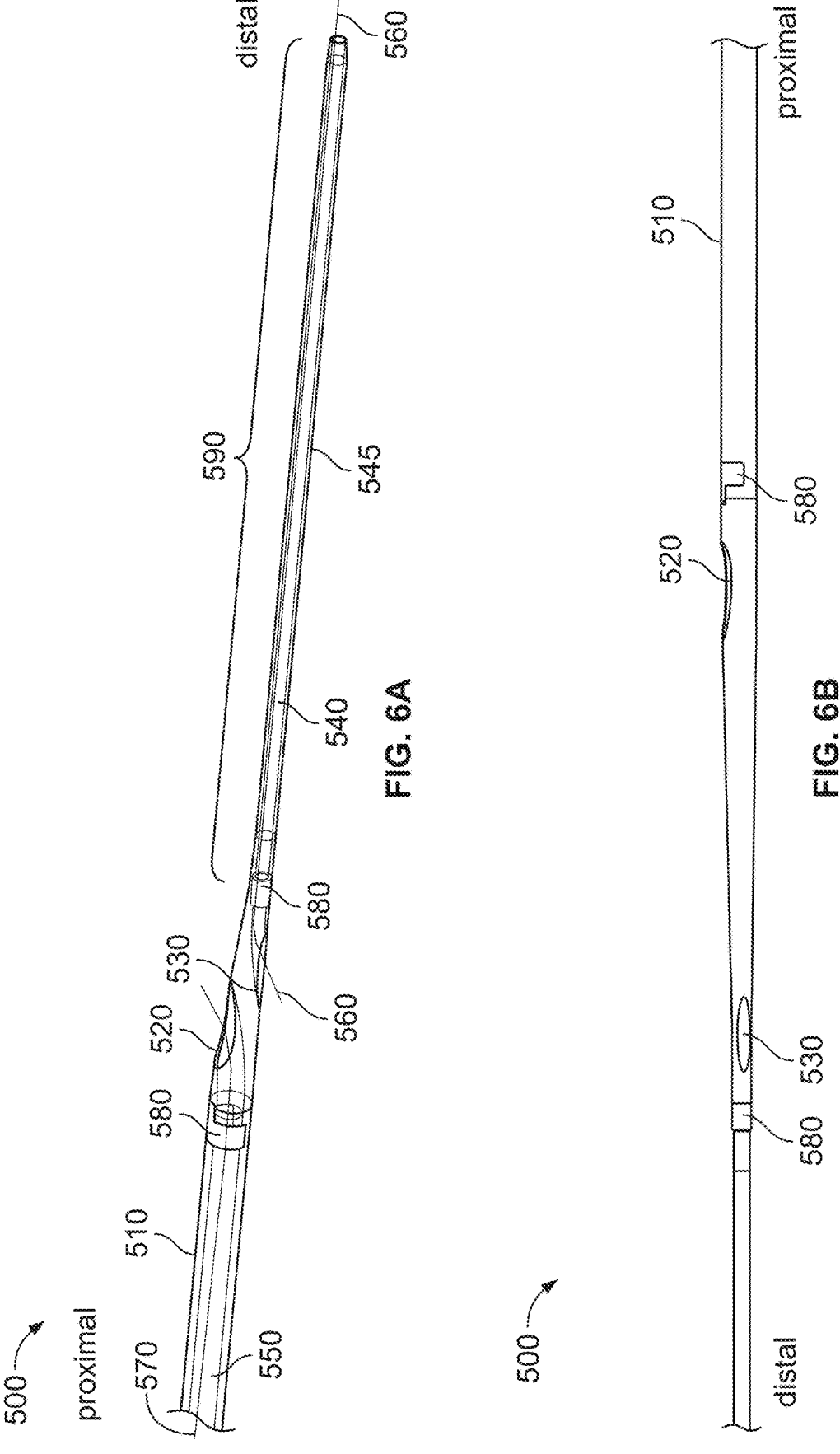
FIGS. 6A and 6B illustrate a puncture system delivery system, according to embodiments.

According to some embodiments described below, rather than locate a puncture system exit port at the distal-most point on a catheter (or proximate the distal-most point), a puncture system exit port can be located proximally from the distal-most point on the catheter. Using such embodiments, the catheter can be advanced until the puncture system exit port nears the desired access point in the patient's anatomy to deploy the puncture system. FIGS. 6A and 6B illustrate two embodiments of such a system 500. The system 500 includes a proximal catheter 510, a puncture catheter lumen 550, a puncture system exit port 520, a distal catheter 545, a distal lumen 540 (having a distal zone 590), a primary navigation guide wire port 530, a puncture system 570, a primary navigation guide wire 560, and radiopaque marker(s) 580. As will be further discussed, a puncture system 570 can include a stylet, a catheter, and/or a puncture system guide wire in embodiments. In embodiments, the puncture system 570 can include a puncture system guide wire and a needle. For example, in an exemplary puncture system 570, a stylet may first be introduced to puncture tissue including a vein wall, interstitial space, and the dura. A catheter may then be advanced over the stylet. The stylet may be removed, and a puncture system guide wire can be introduced. A puncture system guide wire can be used for later access to deliver the CSF shunt. Alternatively, a puncture system 570 could include hollow needle. The hollow needle punctures the tissues, and then a puncture system guide wire can be introduced through the hollow needle. As used herein, the primary navigation guide wire (such as 560) is used to navigate the larger systems (such as system 500), while the puncture system guide wire is part of the puncture system (such as puncture system 570).

The primary navigation guide wire port 530 (which is for the primary navigation guide wire 560) can be distal to the puncture system exit port 520. The primary navigation guide wire port 530 and distal lumen 540 can be configured to accommodate a 0.008" or up to a 0.035" primary navigation guide wire 560. The primary navigation guide wire port 530 is an entrance port where the primary navigation guide wire 560 enters the distal lumen 540 in the distal catheter 545, extends through the distal zone 590, and exits through a distal aperture. The primary navigation guide wire port 530 can be rotationally offset from the puncture system exit port 520 from 30° to up to 180° (at 180° it will be on the opposing side). A rotation of 180° is shown in FIG. 6A. A rotation of 90° with a greater distance between the primary navigation guide wire port 530 and the puncture system exit port 520 is shown in FIG. 6B. The puncture system exit port 520 in the embodiments is shown at an angled exit designed to direct the puncture system posteriorly upon exit. The distal zone 590 can be from 5 mm to up to 20 cm long, for example between 2 cm to 4 cm. The distal catheter 545 facilitates advancing and navigating the system 500 through the intervertebral vein 130 and/or into the epidural venous plexus 140. In addition, and once in place, the distal catheter 545 can also act as a stabilization element or anchor to assist in keeping the system 500 from undesirably moving during puncturing. To further assist in anchoring the distal zone 590, the distal zone 590 can have a balloon (not shown) that can be activated by the surgeon. The balloon can extend from the system distal zone 590 to a vein wall to anchor the system 500. Instead of a balloon, a stent or other type of expansion device could be used to stabilize the distal zone 590 into the epidural venous plexus. Vein orientation with respect to the puncture system exit port 520 can be visualized fluoroscopically with assistance with one or more of the radiopaque markers 580.

Figure 10:
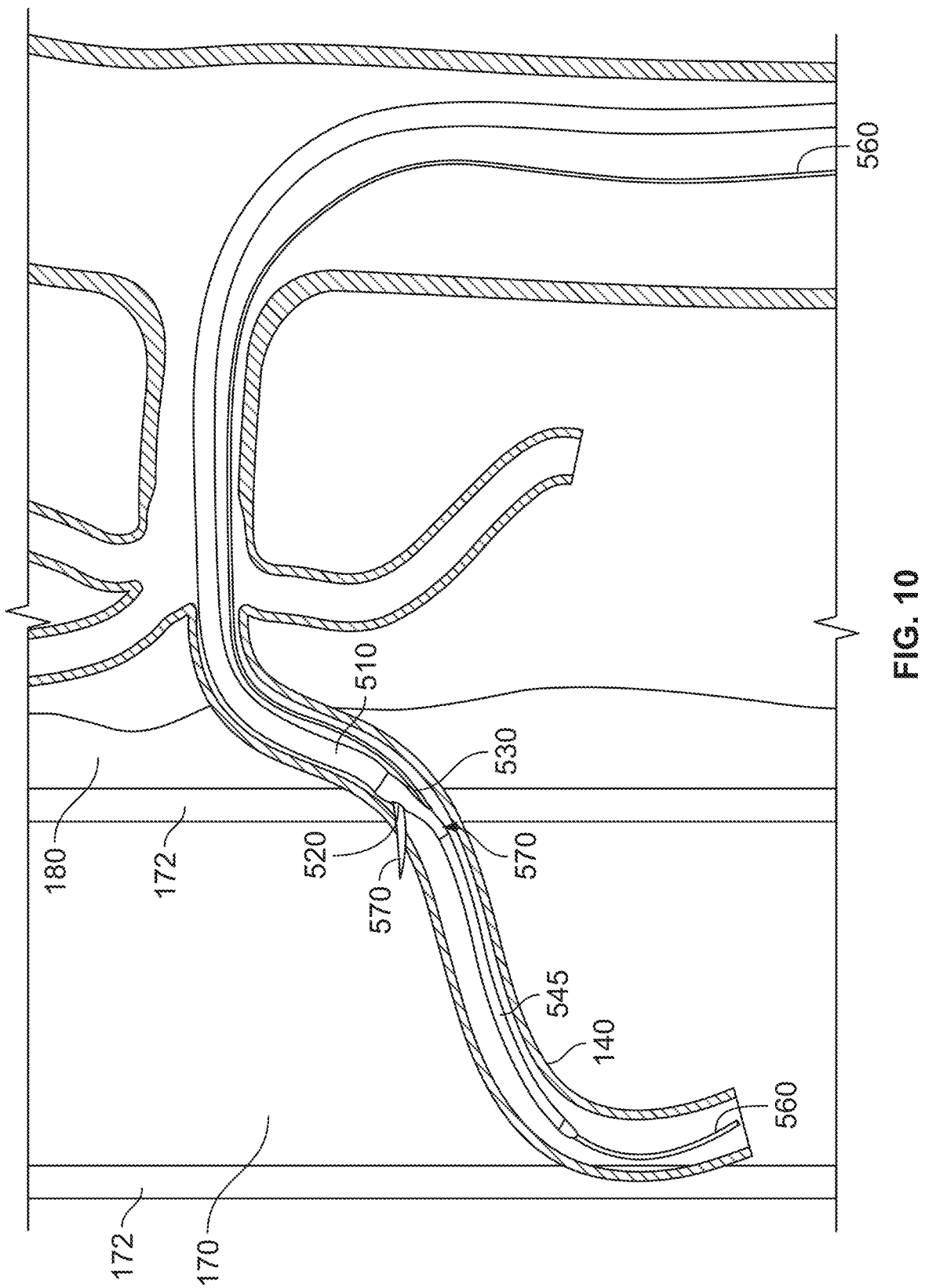
FIG. 10 illustrates a puncture system delivery system being employed to deliver a puncture system to puncture a patient's dura, according to embodiments.

FIG. 10 illustrates the system 500 being used to puncture a patient's dura 172 during a CSF shunt implantation procedure. The system 500 is navigated through the patient's vasculature via the primary navigation guide wire 560, which extends through the primary navigation guide wire port 530 and distal lumen 540. The system 500 is positioned such that the puncture system exit port 520 is suitably located for deployment of the puncture system 570. In the example of FIG. 10, the puncture system exit port 520 is located in the epidural venous plexus 140. The puncture system 570 is directed posteriorly from the puncture system exit port 520 (i.e., into the page) through a patient's dura 172 and into the thecal sac 170.

Figure 7A:
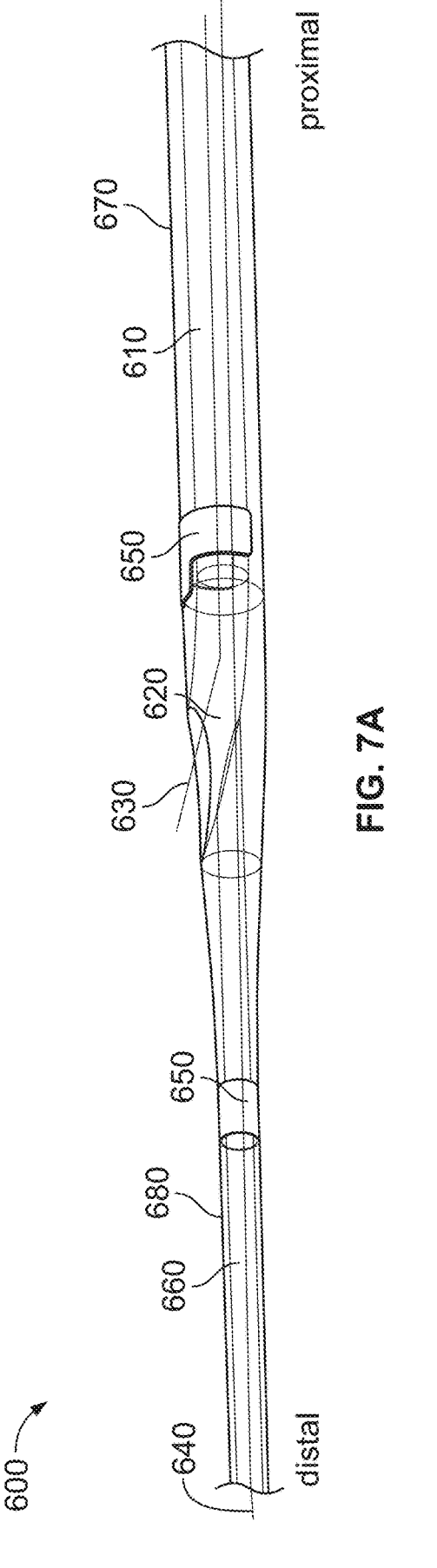
FIGS. 7A and 7B illustrate a puncture system delivery system, according to embodiments.
Figure 7B:
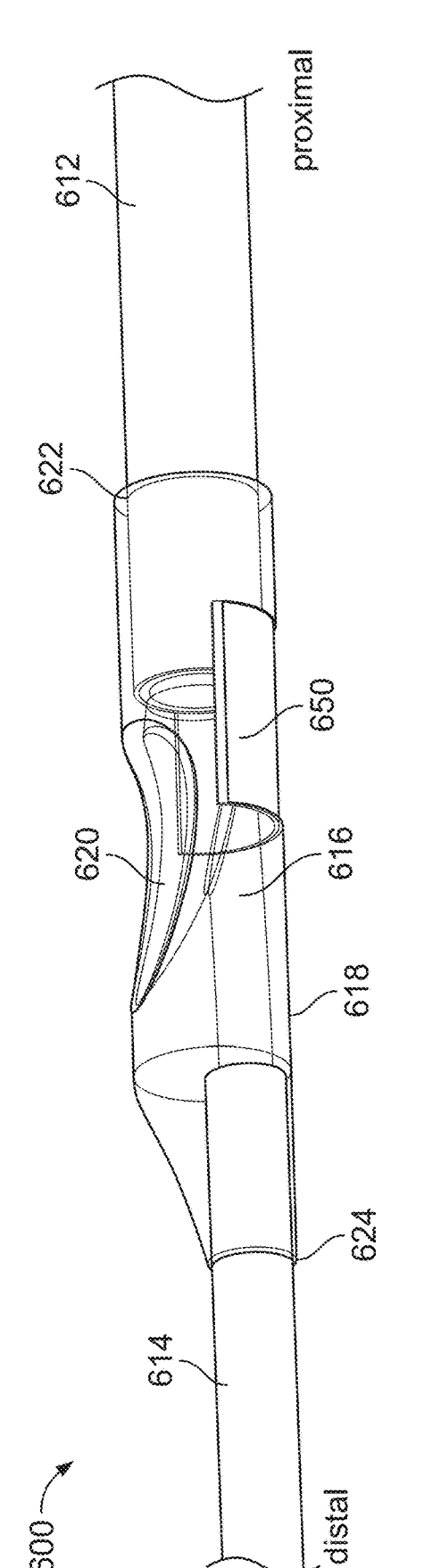

FIGS. 7A and 7B show variations on the embodiments described herein. In the example of FIG. 7A, the system 600 includes a proximal catheter 670 having a proximal lumen 610, a puncture system exit port 620, a puncture system 630, a primary navigation guide wire 640, radiopaque marker(s) 650, and a distal catheter 680 having a distal lumen 660. The radiopaque marker(s) may be located on the proximal catheter 670 and/or the distal catheter 680. In the proximal region, the puncture system 630 and the primary navigation guide wire 640 both pass through the same shared, proximal lumen 610. The puncture system 630 is received by the puncture system exit port 620 such that at least a portion of the puncture system 630 exits the system 600 through the puncture system exit port 620, while the primary navigation guide wire 640 continues onward through the distal lumen 660. The puncture system exit port 620 is in communication with the proximal lumen 610 (e.g., continuous with).

The distal lumen 660 is in communication with the proximal lumen 610. The distal lumen 660 can be configured to accept the primary navigation guide wire 640 and reject the puncture system 630. The diameter of the distal lumen 660 can be too small to accept the puncture system 630, but large enough to accept the primary navigation guide wire 640, such that the primary navigation guide wire 640 is accepted by the distal lumen 660 and the puncture system 630 is not able to enter the distal lumen 660. The diameter of the proximal lumen 610 may be greater than the diameter of the distal lumen 660. The diameter of the proximal lumen 610 may be greater than 0.024 inches. The diameter of the distal lumen 660 may be less than 0.020 inches. The diameter of the puncture system exit port 620 may be greater than the diameter of the distal lumen 660. The diameter of the puncture system exit port 620 may be the same as the diameter of the proximal lumen 610 where the puncture system exit port 620 and the proximal lumen 610 meet.

Further, the primary navigation guide wire 640 can block access to the puncture system exit port 620 by the puncture system 630. Therefore, the primary navigation guide wire 640 may need to be retracted proximally from the puncture system exit port 620 before the puncture system 630 can be advanced therethrough.

The variation of FIG. 7B is similar to the embodiment of FIG. 7A but shows a proximal catheter 612 and a distal catheter 614 connected by a connector 618. The connector 618 may have a proximal recess 622 configured to accept the proximal catheter 612 and a distal recess 624 configured to accept the distal catheter 614. The connector 618 may include a puncture system exit port 620, a distal passageway 616, and radiopaque marker(s) 650. The distal passageway 616 extends between the puncture system exit port 620 and the lumen of the distal catheter 614. The diameter of the distal passageway 616 may be the same as the diameter of the lumen of the distal catheter 614. The diameter of the distal passageway 616, like that of the distal lumen 660, may be too small to allow the puncture system 630 to enter into the distal lumen 660. Instead, the puncture system 630 is guided through the puncture system exit port 620 and out of the system 600.

The system 600 can accommodate guide wires for 0.008" up to 0.035" such as 0.012", 0.014" and/or 0.018". The proximal lumen 610 accepts a puncture system 630. Primary navigation guide wire 640 can transverse through the system 600 and out the distal end of the system 600.

In the case that a needle is used for the puncture system 630, once proper placement and orientation of the system 600 is confirmed via fluoroscopy, the primary navigation guide wire 640 can then be retracted back into the needle (in the proximal lumen 610), positioning the primary navigation guide wire 640 just proximal to the needle tip. The needle of the puncture system 630 can then be advanced out of the puncture system exit port 620. After puncturing the vessel wall, interstitial tissue, and dura wall with the needle of the puncture system 630, a guide wire of the puncture system 630 can be advanced through the needle/cannula lumen into the thecal sac 170, extending either cranially or caudally in the thecal sac 170 to serve as a track to deliver subsequent catheters. The needle can then be withdrawn from the patient, allowing the shunt assembly or delivery sheath to be advanced into position over the guide wire of the puncture system 630.

In another embodiment, a catheter can be used in the puncture system 630. The catheter of the puncture system 630 can accept a small stylet and/or needle that may be used within the proximal lumen 610 and puncture system exit port 620. The catheter of the puncture system 630 can have an outer diameter that is larger than the inner diameter of the distal lumen 660, thereby preventing the catheter of the puncture system 630 from entering the distal lumen 660 small enough to pass out of the puncture system exit port 620.

Figure 8:
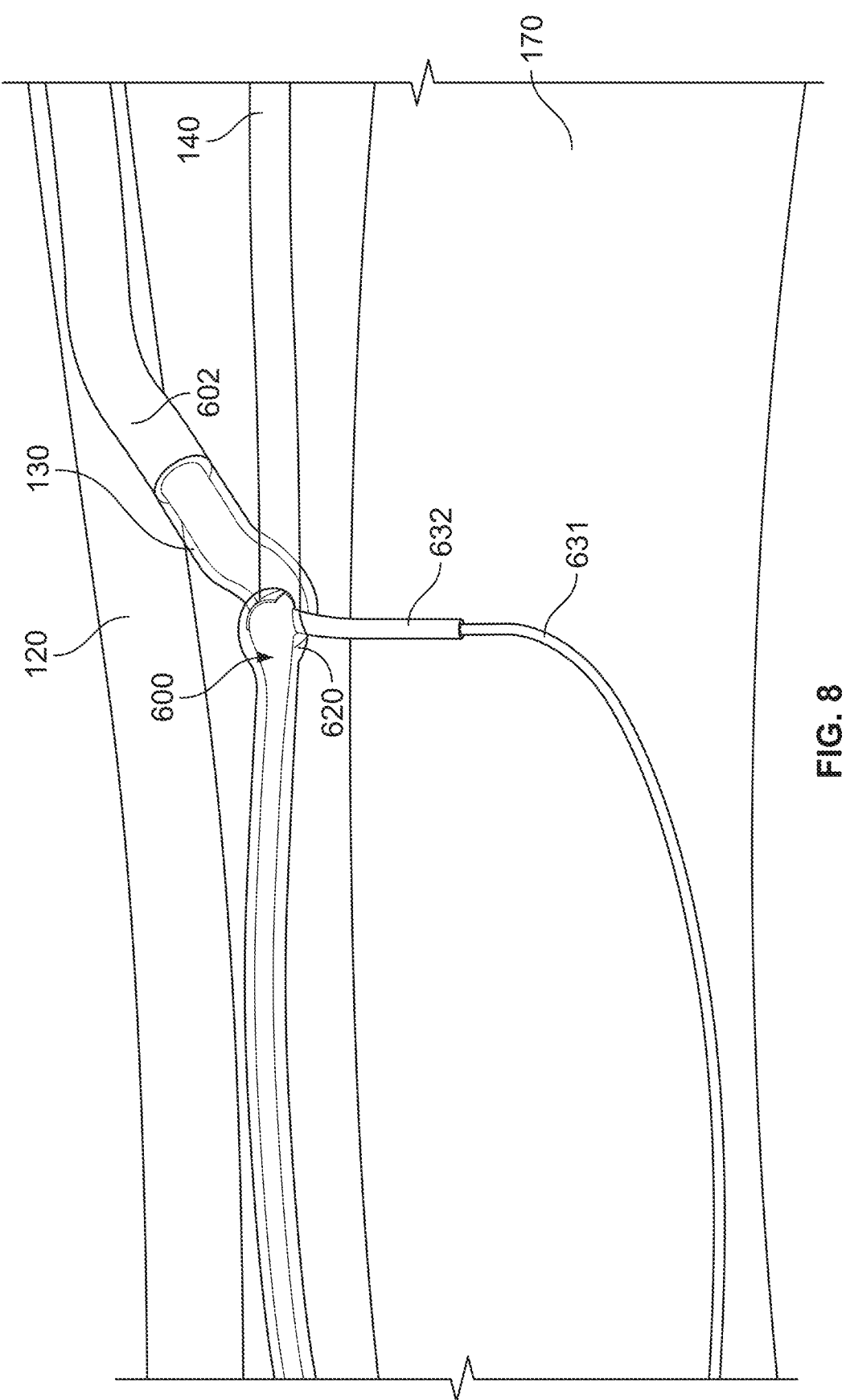
FIG. 8 illustrates the use of a puncture system delivery system to deliver a puncture system, according to embodiments.

FIG. 8 illustrates the use of system 600 to deliver a puncture system 630, according to embodiments. The system 600, which navigates through the patient's vasculature over a primary navigation guide wire 640 (not shown) and through a guide catheter 602 is positioned until the puncture system exit port 620 is suitably located. The primary navigation guide wire 640 may then be retracted such that it does not block the puncture system exit port 620. A catheter 632 of the puncture system 630 can be advanced through the system 600 and out of the puncture system exit port 620. A stylet or needle (not shown) can be passed through the catheter 632 to puncture the vessel wall, interstitial space, and dura. The catheter 632 can then be advanced over the stylet or needle (not shown) and into the thecal sac 170. The catheter 632 can dilate the tissues along the puncture pathway (vessel wall, interstitial space, and dura). Once the catheter 632 is intrathecal, the stylet or needle can be retracted. The surgeon can then aspirate CSF or inject radiopaque contrast agents from/into the thecal sac to confirm that the distal end of the catheter 632 is intrathecal. A guide wire 631, such as a 0.014"-0.018" guidewire, could be advanced through the catheter 632 into the thecal sac 170 to aid in advancing subsequent catheters, such as dilatation catheters and the CSF shunt.

An alternative approach to dilate the tissue after initial puncturing with a stylet or needle is to advance a balloon over the guide wire 631 to traverse the vessel-to-thecal sac 170 pathway, thereby dilating the tissues (e.g., vessel wall(s), interstitial space, and/or dura) to thereby dilate the passageway. The balloon outer diameter can range from 0.75 mm to 2 mm with, for example a range of 1.25 mm to 1.5 mm outer diameter when inflated, and/or a length between 3 mm to 15 mm. The balloon can be a stand-alone component or integrated with the guide wire 631.

Figure 12:
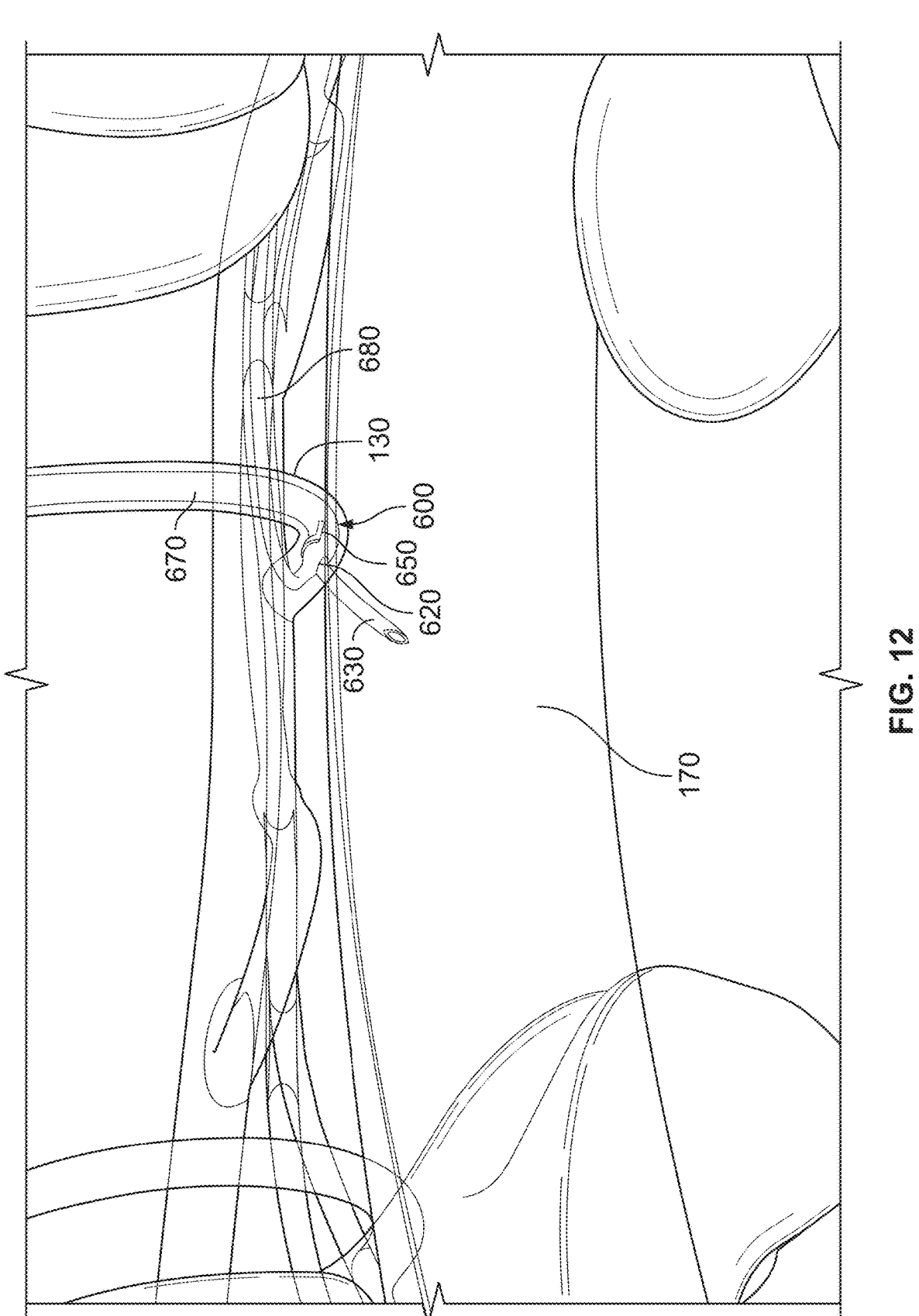
FIG. 12 illustrates a puncture system delivery system being employed to deliver a puncture system to puncture a patient's dura, according to embodiments.

FIG. 12 shows an example of the system 600 delivering a puncture system 630 to puncture the dura to enter the thecal sac 170. In this example, the puncture system 630 is shown to include a hollow needle, which punctures the vein wall, interstitial space, and through the dura. After the hollow needle has punctured these layers and gained access to the thecal sac 170, the lumen of the needle can be used to introduce devices, fluids, or drugs into the cerebral spinal fluid area. As an example, the hollow needle could be used to introduce a guide wire in the puncture system 630 to advance subsequent devices into the thecal sac 170. The hollow needle could also be used to extract cerebral spinal fluid, or measure pressure in the area, for example. Puncture system 630 may take various forms and may also include a catheter, solid stylet, cannula, guide wire, and/or any combination of the above. Examples of potential puncture systems 630 are disclosed and are interchangeable to be used with variations of system 600.

Figures 9A, 9B, 9C:
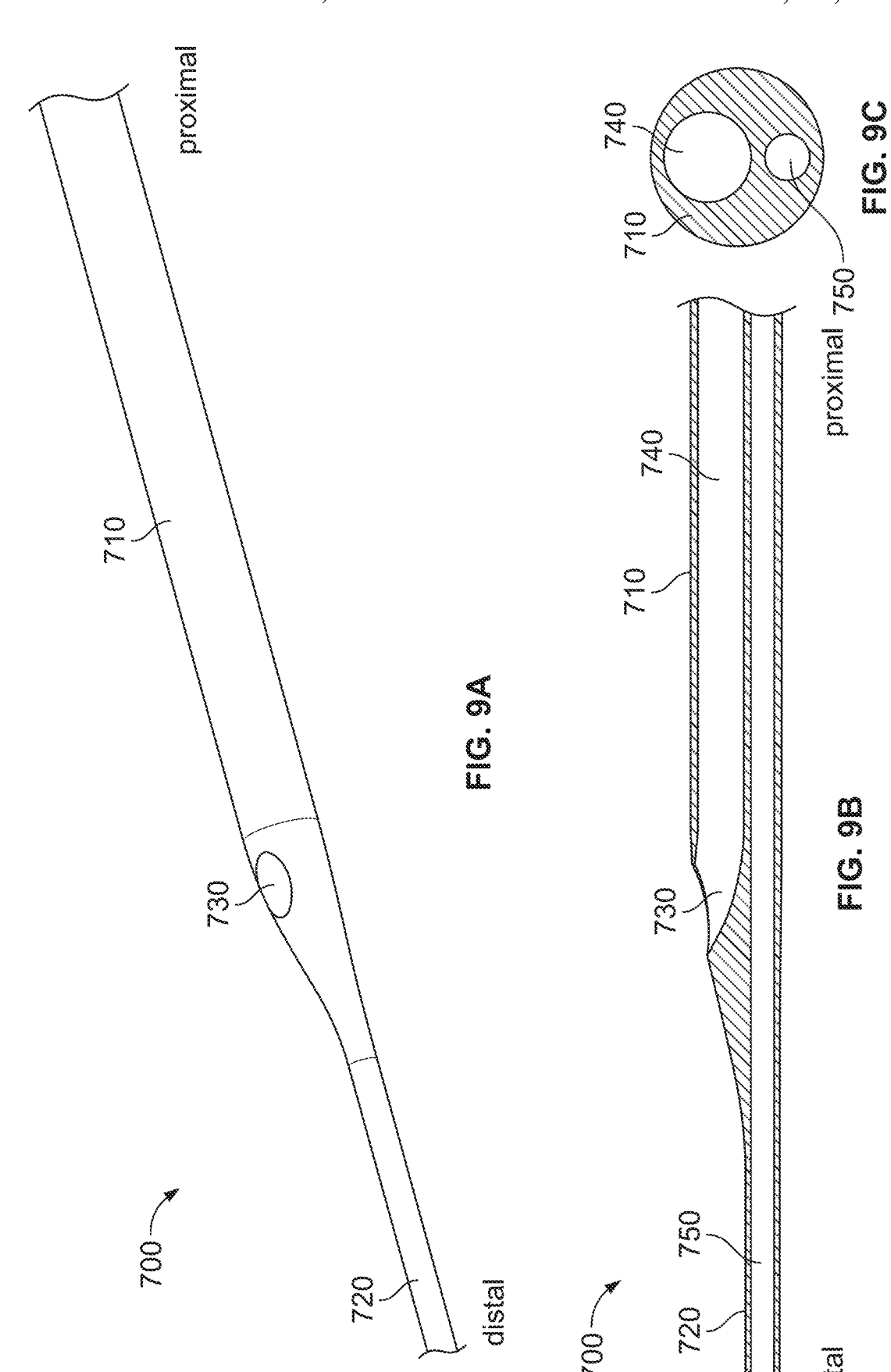
FIGS. 9A-9C illustrate a puncture system delivery system, according to embodiments.

FIGS. 9A-9C illustrate a system 700 that is a variation of the system 600. Instead of having a shared lumen, however, the system 700 has separate lumens for the guide wire and the puncture system. FIG. 9A shows an exterior perspective view of the system 700. FIG. 9B shows an axial cross-sectional view of the system 700. FIG. 9C shows a radial cross-sectional view of a proximal region of the system 700. The system 700 can include a proximal shaft 710, a distal shaft 720, a guide wire lumen 750, a puncture system lumen 740, and a puncture system exit port 730. The guide wire lumen 750 is configured to accommodate the guide wire, while the puncture system lumen 740 is configured to accommodate the puncture system. The guide wire lumen 750 and the puncture system lumen 740 are separate and not in communication with each other, or at least not in communication such that the guide wire and/or puncture system could cross over into the other one's lumen. The guide wire lumen 750 and the puncture system lumen 740 may both extend through the proximal shaft 710. Only the guide wire lumen 750 may extend to the distal shaft 720. The puncture system lumen 740 may terminate at the puncture system exit port 730. System 700 can allow the surgeon to utilize the puncture system exit port 730 and the guide wire lumen 750 concurrently.

Another variation could combine the system 600 with the system 300. In this configuration, the physician could use the distal catheter 680 and distal lumen 660 to catheterize the applicable veins in conjunction with steerability provided by a pull wire 330 located in the proximal catheter 670. The steerability could also provide support in the vasculature after the system is articulated within the vasculature.

As discussed, puncture systems can include needles or stylets. Shaft construction of such needles or stylets may have a range of variable flexibility at various locations to navigate the tip through the delivery system and exit through the angled configurations, as well as to maintain having the required axial stiffness and push ability to puncture the vein wall, interstitial space, and dura wall to advance the system into the thecal sac. A shaft can include multi-filar tubing, laser-cut hypo tube, braided tubing, laser cut hard plastic, and/or the like. The shaft may be straight or include variable and different bend radius(es) at different exemplary locations (either sectioned or integral), which can be helpful for transversing tight bend radiuses in the venous system while maintaining push ability of the tip. A distal section segment, or region of the system, configured to be located in a region at or near where the needle or puncturing system is exiting catheter side exit port into thecal sac may have a bend radius of between 3 mm to 15 mm, for example between 5 mm to 7 mm. A mid-section, segment, or region of the system configured to be located in a region at or near where the needle shaft turns from an ascending lumbar vein into an intervertebral vein may have a bend radius of between 10 mm to 30 mm, for example about 15 mm. A proximal section, segment, or region of the system configured to be located in a region at or near where the needle shaft is turning from iliac vein and into the lumbar vein may be between 10 mm to 45 mm, for example about 20 mm.

In embodiments, a stylet may have custom curves to preferentially orient the sharp tip within the anatomy. Examples of such stylets are disclosed in U.S. application Ser. No. 19/177,127, filed Apr. 11, 2025, the entirety of which is incorporated by reference herein. The '127 application discloses stylets in two or more planes, such as a bi-plane stylet. Such stylets are within the scope of the present application. For example, a stylet may have two curves along its length that are in planes approximately 90° from each other but may vary from 60° to 120°. The first (proximal) curve may have a geometry that follows the curvature of connecting veins (the ascending lumbar vein and intervertebral vein, for example). The second curve may be oriented in a plane offset from the first curve such that when the first curve follows the venous anatomy, the second curve orients the tip in a posterior direction for thecal sac puncture. The first curve serves to orient or "clock" the stylet in the appropriate position with the anatomy, so the second curve is automatically directed posteriorly with respect to the axis of the vein, without the need for surgeon control. When used in tandem with any of the catheters described herein, the multi-plane stylet provides additional posterior direction to divert the sharp tip out the vein wall, across the interstitial tissue, and through dura wall.

FIGS. 11A-11E depict exemplary needles and stylets, either integral and/or attached to different flexible constructed proximal shafts, according to embodiments. As will be understood, the features in the different embodiments can be selected in different combinations. The laser cut and coil/wire wound shafts can be sealed either by an internal or exterior coating or liner to allow for the surgeon to flush saline and/or contrast into the thecal sac, or aspirate CSF fluid after puncture. The depicted puncture tips (needle, trocar, and/or shovel shape) can be relatively short, such as between 1 mm to 8 mm, for example between 2 mm to 6 mm. The attachment (the needle tip attached to a flexible region) can be welded, adhesive, or heat bonded. The puncture tip could also be incorporated directly into the shaft as a single component (i.e., no attachment). The puncture tip can be a biocompatible metal, such as stainless steel, Nitinol, or a hard rigid plastic. The needle lumen inner diameter can be large enough to accommodate a 0.008" guide wire up to a 0.035" guide wire.

Figures 11A, 11B:
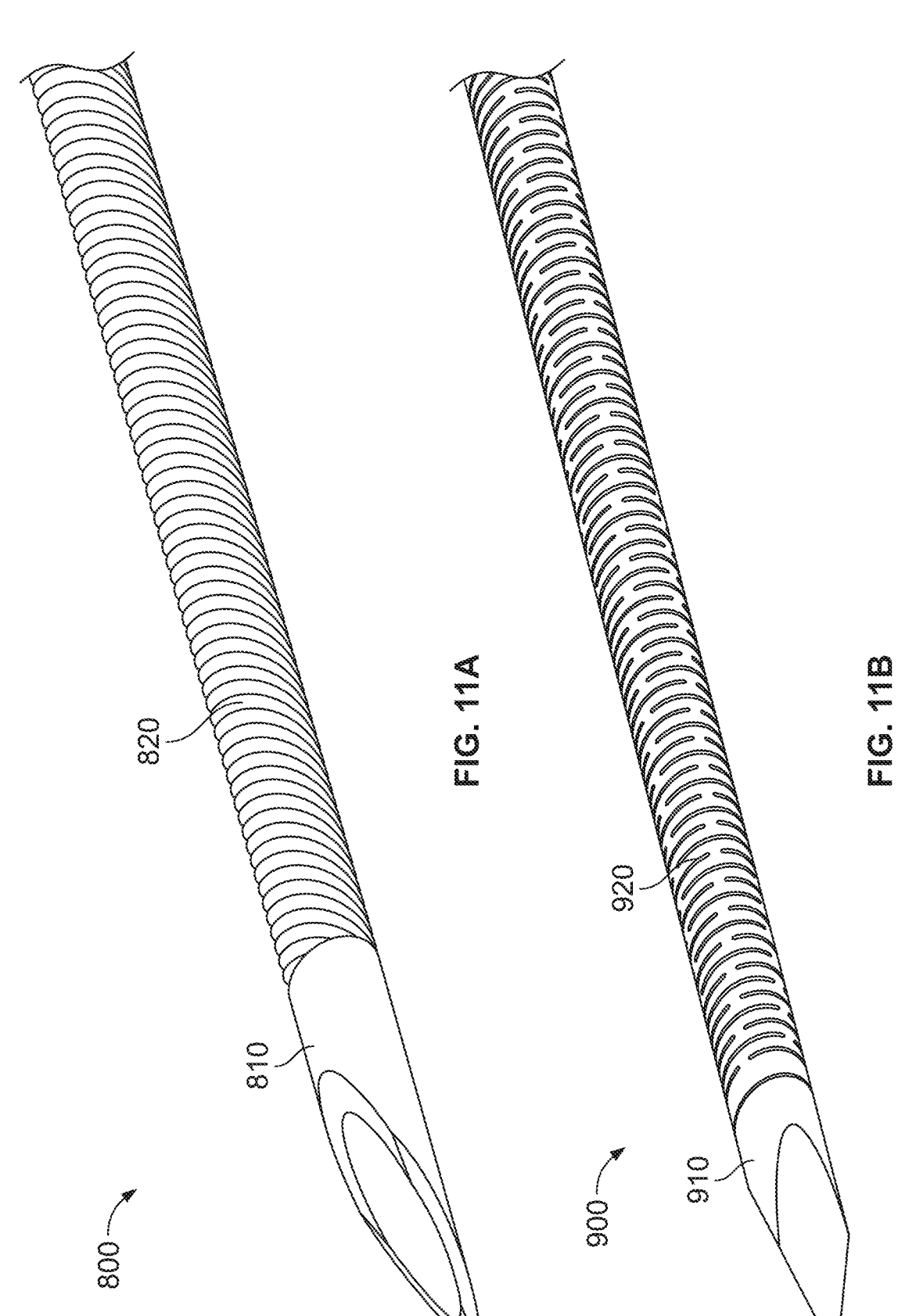
FIGS. 11A-11E illustrate exemplary needles and stylets part of puncture systems, according to embodiments.

FIG. 11A illustrates a needle 800 including a tip 810 and a body 820. The needle 800 is hollow. The tip 810 has a beveled end. The body 820 is shown as a coil, and may be a multi-filar coiling. The body 820 and the tip 810 may be attached, for example, by a weld.

FIG. 11B illustrates a stylet 900 including a tip 910 and a body 920. The body 920 may be a laser-cut rod or a hypo-tube. The tip 910 may have a trocar end. The body 920 flexibility can be varied by laser cut patterns. The tip 910 may be integral with the body 920, or, as shown, the tip 910 can be separate from the body 920. The tip 910 can be attached to the body by welding or a weld.

Figure 11C:
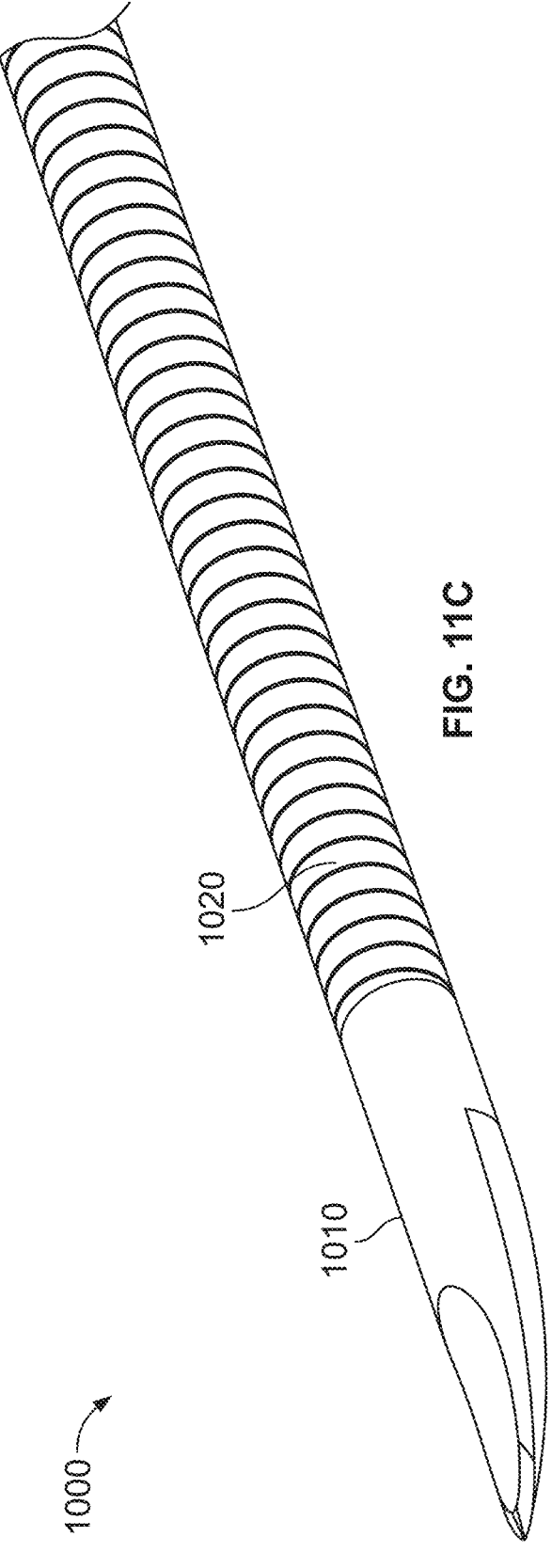

FIG. 11C illustrates a needle 1000 including a tip 1010 and a body 1020. The body can be a flat-wire coil tube. The tip 1010 can have a shovel-shaped tip. The tip 1010 can be welded to the body 1020 or can be integral with the body 1020.

Figure 11D:
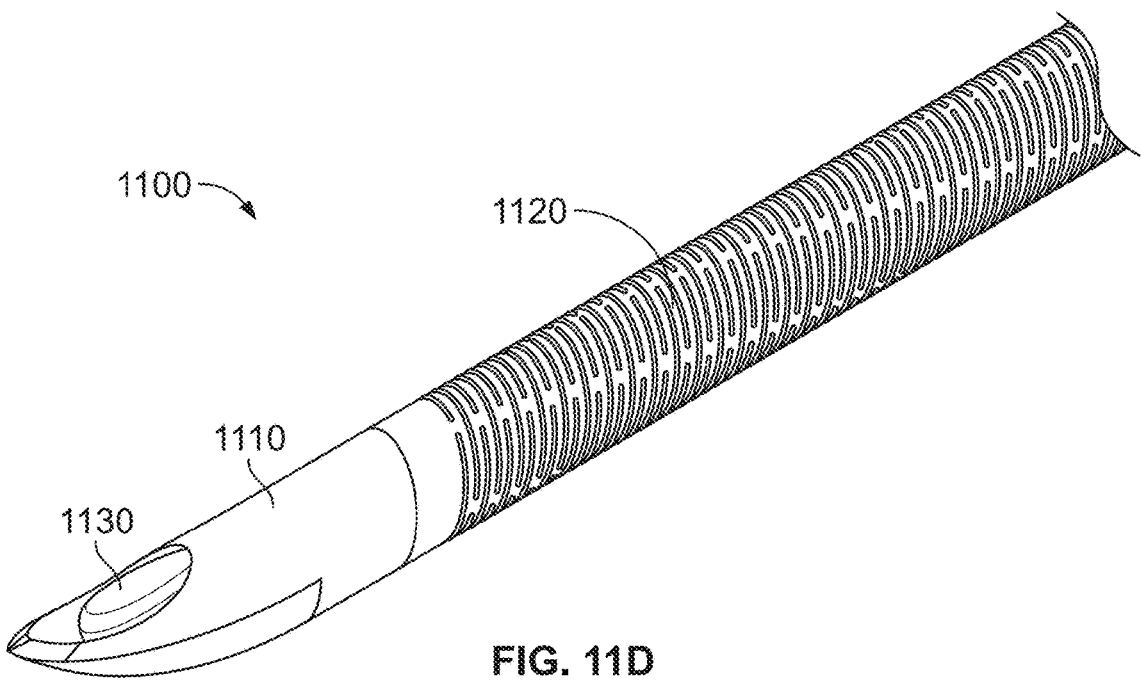
Figure 11E:
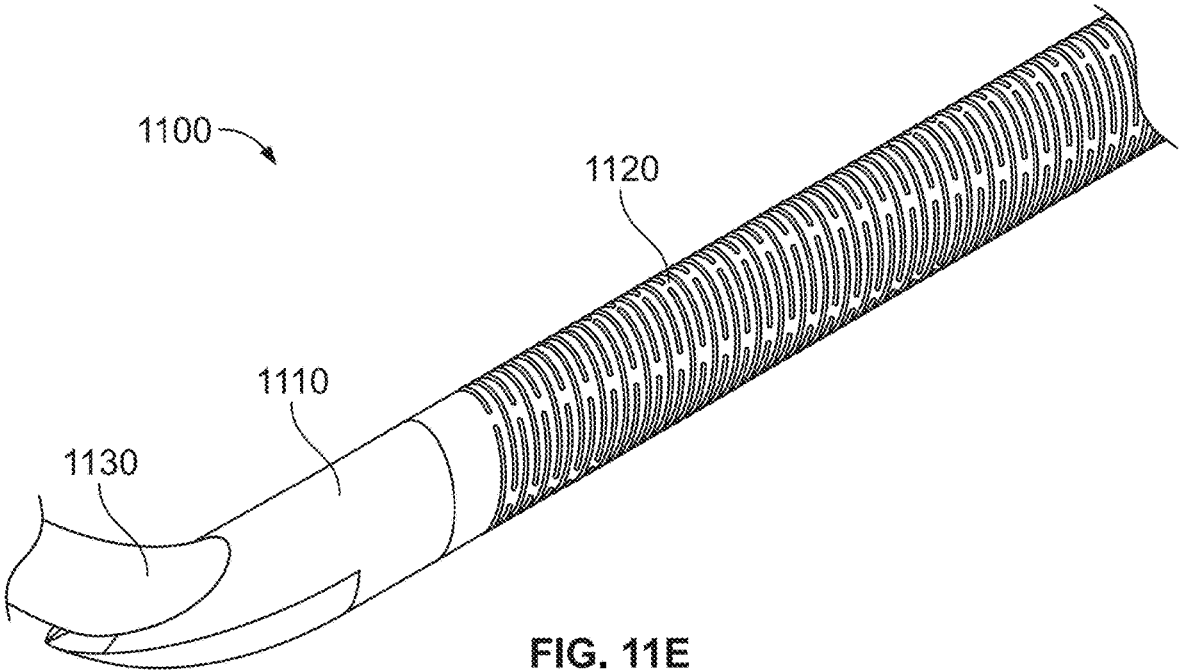

FIG. 11D illustrates a needle 1100 including a tip 1110 and a body 1120. The body 1120 is a laser-cut hypo-tube. The tip 1110 is shovel-shaped. A hybridized stylet/guide wire 1130 is shown in the tip 1110 (but extends through the needle 1100). The hybridized stylet/guide wire 1130 has a semi-rounded tip with a slight flat surface on the outer side, allowing it to function as both a guide wire and a stylet. The hybridized stylet/guide wire 1130 could be used to fill the inner lumen of the tip 1110 during puncture to avoid coring of tissue, acting as a standard needle stylet. The hybridized stylet/guide wire 1130 could then be introduced out of the tip 1110 and act as a guidewire for future catheterizations due to its semi-rounded, atraumatic tip. FIG. 11E illustrates the hybridized stylet/guide wire 1130 extending out of the tip 1110 of the needle 1100.

Figure 13A:
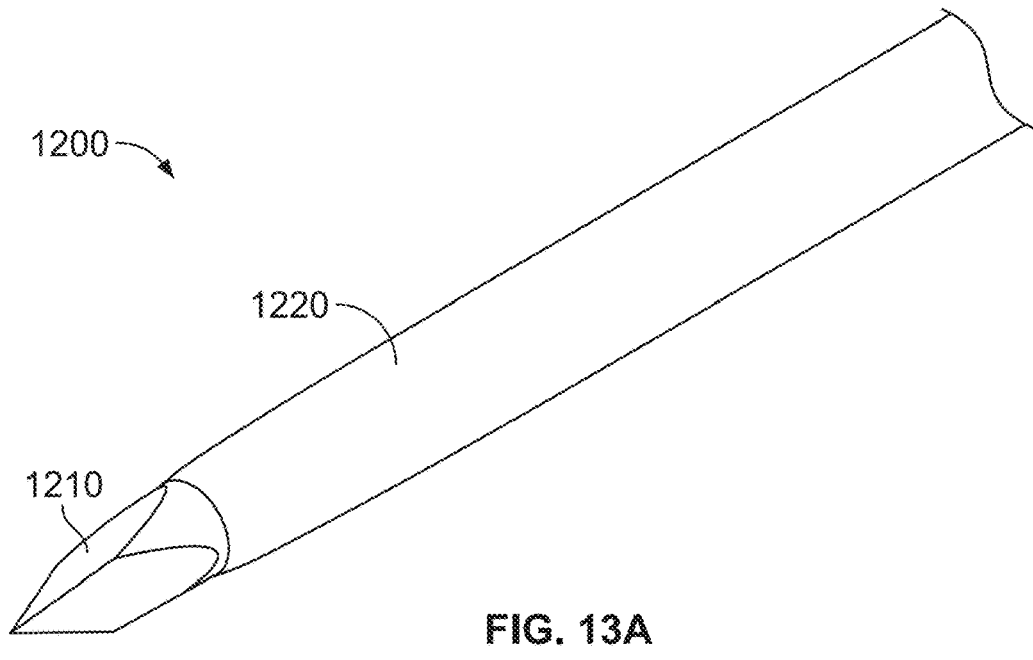
FIGS. 13A-13C illustrate a stylet system, according to embodiments.
Figure 13B:
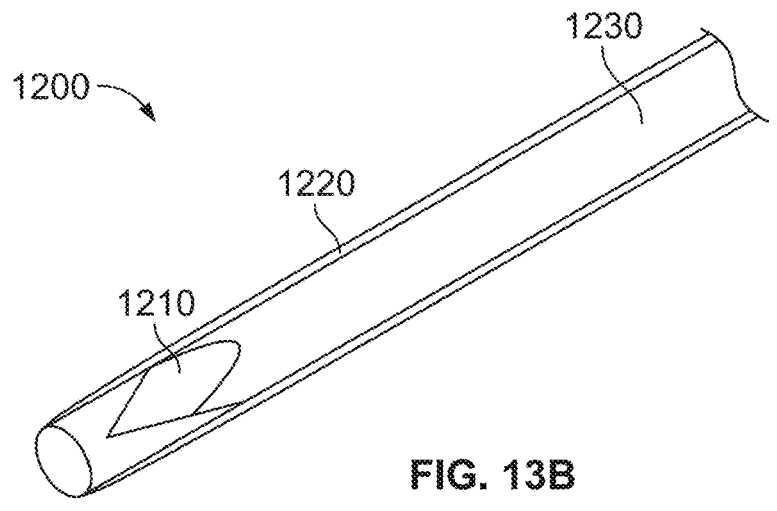
Figure 13C:
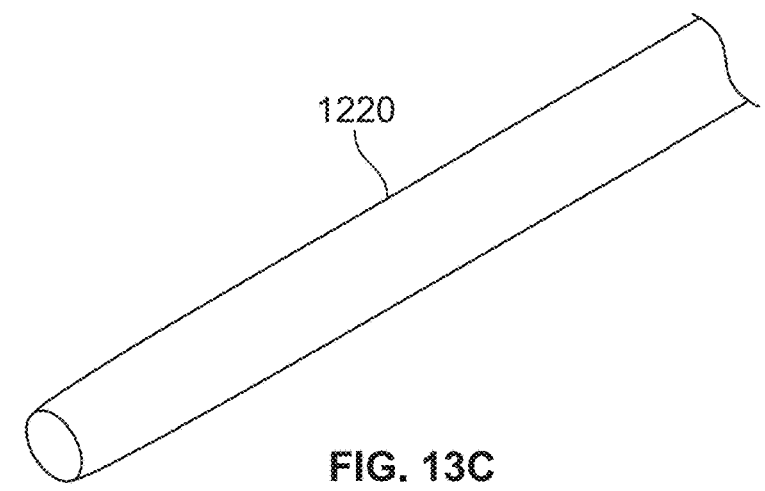

FIGS. 13A-13C show another embodiment, in which a stylet system 1200 includes a stylet tip 1210, a stylet body 1230, and a hollow shaft 1220. FIG. 13B is a transparent view. The stylet tip 1210 may be attached to or integrated with the stylet body 1230. The stylet tip 1210 and stylet body 1230 may extend through the hollow shaft 1220. The stylet tip 1210 is exposed when traversing the vein wall, interstitial tissue, and dura wall. Then, the surgeon may be able to retract the stylet tip 1210 into the hollow shaft 1220, such that the stylet system 1200 may act as a guide wire once it is intrathecal. This design may enable subsequent catheters to be passed over the stylet system 1200 for delivery of devices or drugs without exposing the intrathecal nerves to the sharp stylet tip. The mechanism of retraction may be a mechanical slide, pully, or spring actuated system, for example.

Figure 14B:
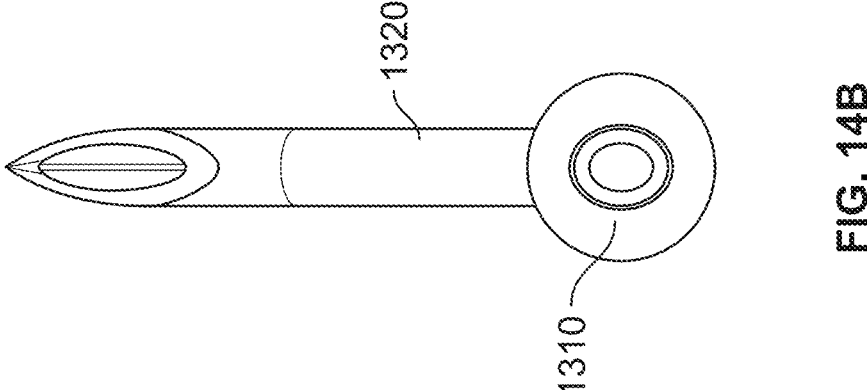
FIGS. 14A and 14B illustrate a puncture system delivery system, according to embodiments.
Figure 14A:
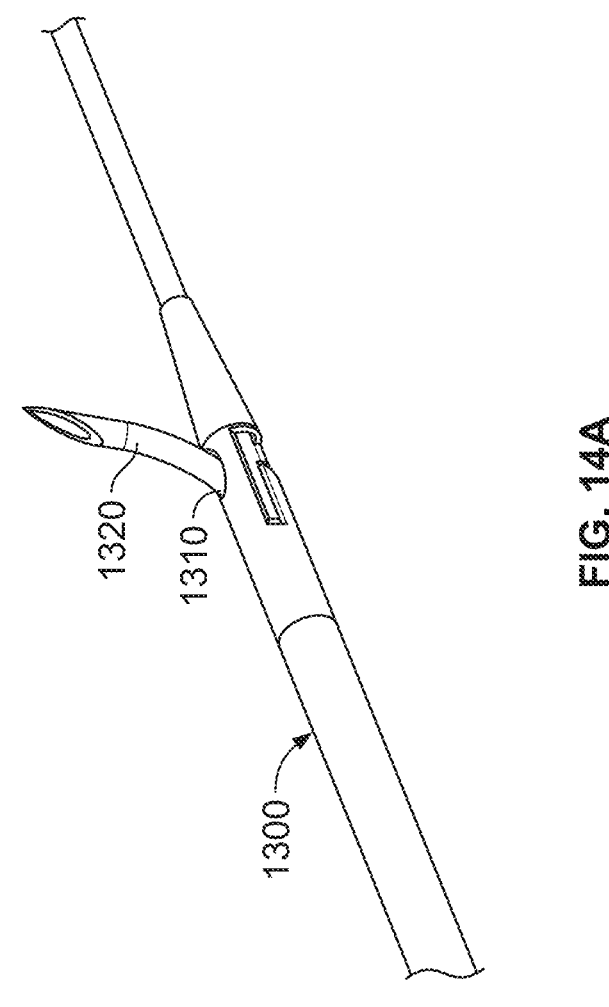

FIGS. 14A and 14B illustrate another embodiment of a system 1300 similar to systems that deliver puncture systems described herein. The system 1300 includes an aperture 1310 in a puncture system exit port, through which a puncture system 1320 extends. In the example shown, the puncture system 1320 is shown as a needle. The inner contour of the aperture 1310 and/or the outer cross-sectional contour of the puncture system 1320 may be such that axial rotational movement of the puncture system 1320 is inhibited. In the example shown, both the inner contour of the aperture 1310 and the outer cross-sectional contour of the puncture system 1320 are complementary ovals, which thereby inhibit axial rotation of the puncture system 1320 relative to the system 1300. Other suitable contours may be used, such as rectangles, triangles, other polygons, irregular shapes, and/or the like. The contours need not match, so long as they inhibit axial rotation of the puncture system 1320 with respect to the system 1300. In this example, the needle shaft may be manufactured with a bend preferentially direct the sharp tip in a posterior direction as it exits the puncture system exit port. Constraining the needle (or stylet) ensures that the bent tip cannot rotate into an anterior or medial direction.

Figure 15:
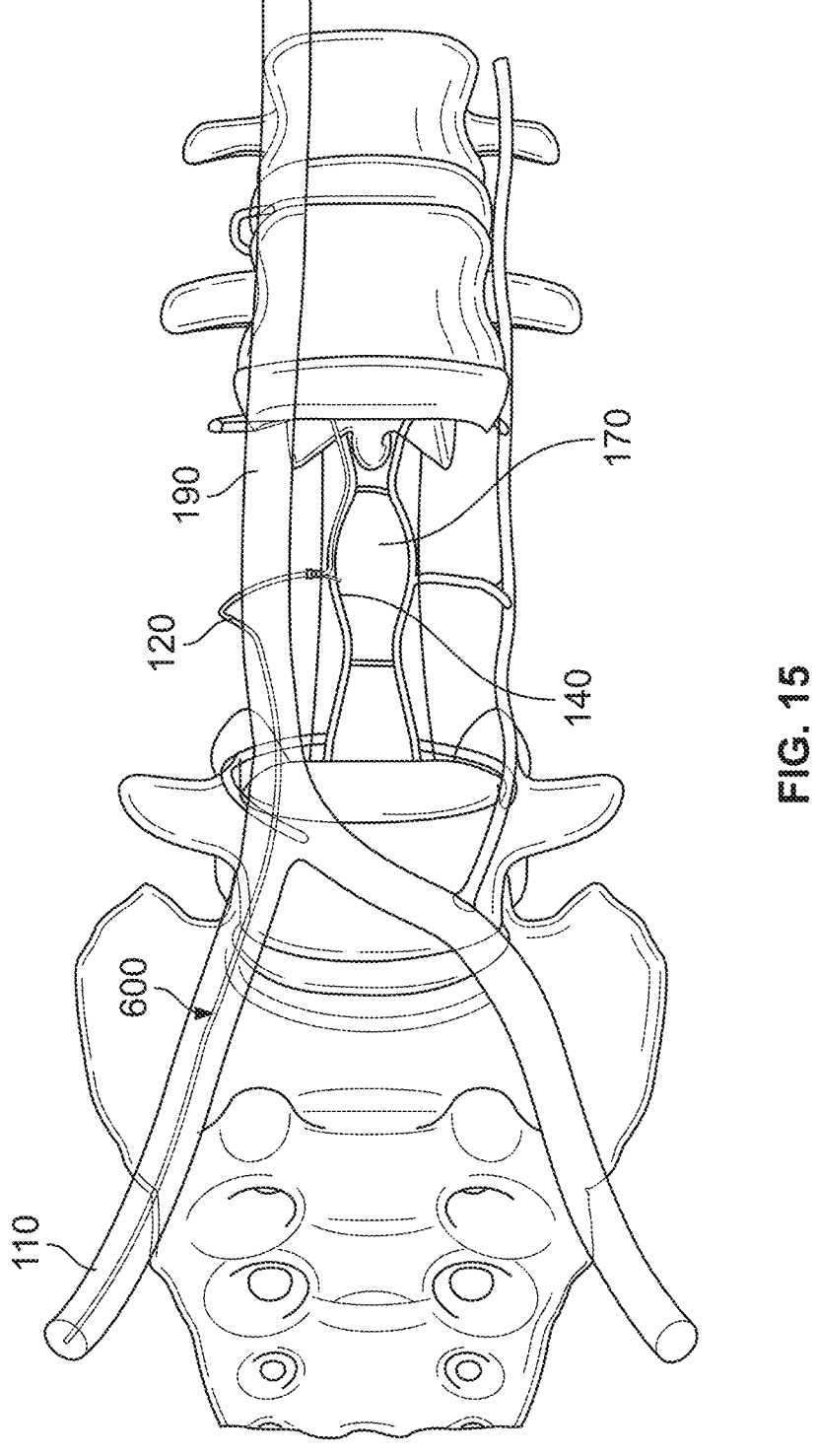
FIG. 15 illustrates the use of a puncture system delivery system and puncture system in a patient's anatomy, according to embodiments.
Figure 16:
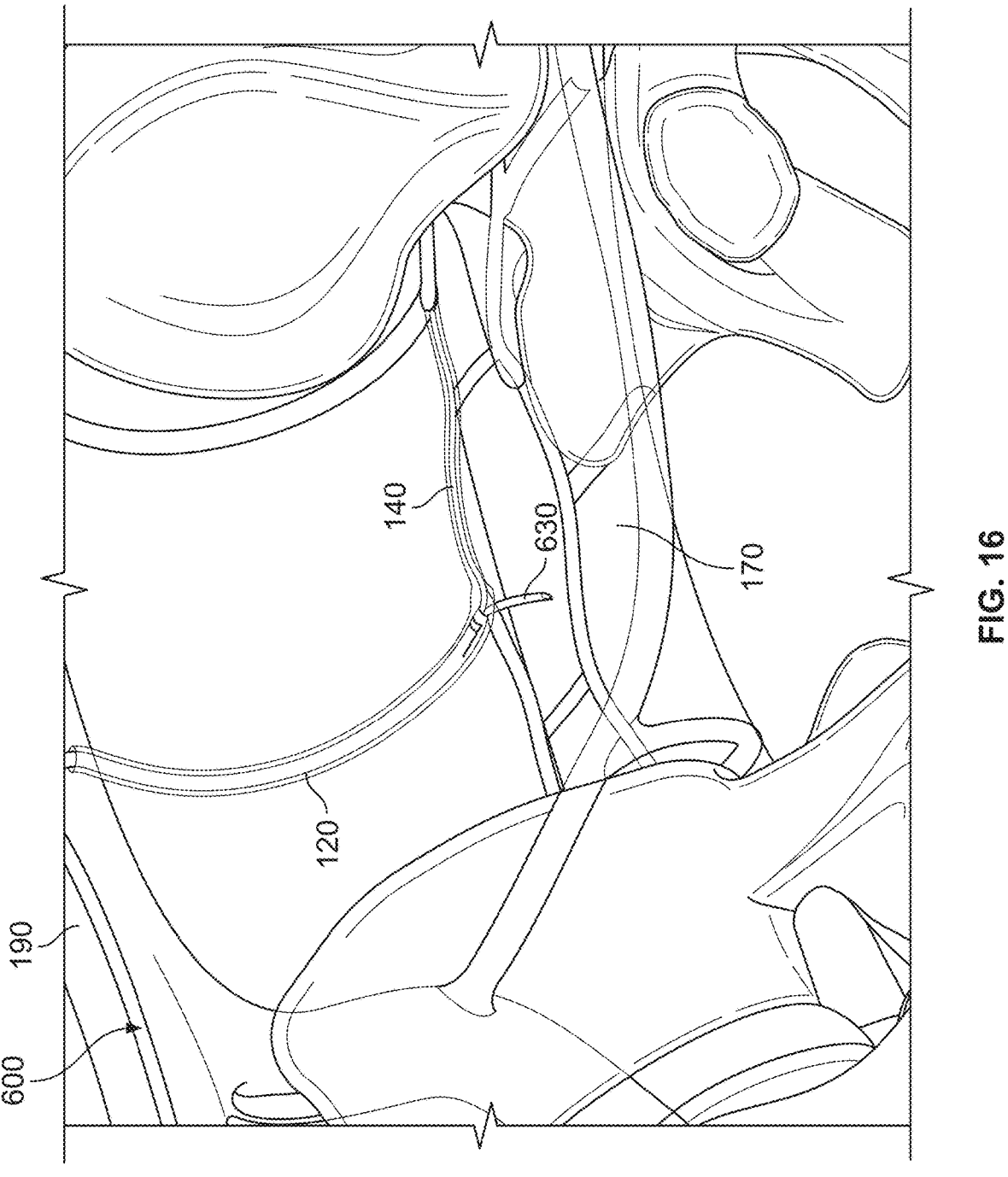
FIG. 16 illustrates the use of a puncture system delivery system and puncture system in a patient's anatomy, according to embodiments.

As shown in FIGS. 15 and 16, a puncture system delivery system, such as system 600, could also approach the thecal sac 170 from the right side of the patient's anatomy. Another example of an anatomical variant in the lumbar vessel anatomy is the absence or partial absence of a left or right ascending lumbar vein. In these anatomies, the ascending lumbar veins 120 are directly connected to the inferior vena cava 190, providing a connection between the inferior vena cava 190, the intervertebral vein 130 and finally the epidural venous plexus 140. The system 600 could also be tracked along this anatomical variant and puncture the thecal sac 170.

Radiopaque markers can inform the surgeon on rotational orientation of the puncture system delivery system and/or puncture system within the vasculature to ensure the puncture system exit port is properly oriented (e.g., facing posteriorly). In other words, the radiopaque markers of the type disclosed herein provide information to the surgeon during fluoroscopy to allow the surgeon to understand the orientation of the puncture system delivery system and particularly the puncture system exit port before and/or during delivery of the puncture system. These radiopaque markers may provide feedback to the physician during the implantation procedure as the physician rotates the delivery system (300, 400, 500, 600, or 700) to orient it into the appropriate position.

FIGS. 17A-17D show various radiopaque markers in different configurations on different puncture system delivery systems, although other configurations are possible as will be understood, such as various combinations of the embodiments depicted and described. The radiopaque markers can be embedded in or on the outer surface of the systems. The radiopaque markers can indicate the puncture system exit port location in the patient's anatomy during a procedure.

Figures 17A, 17B, 17C, 17D:
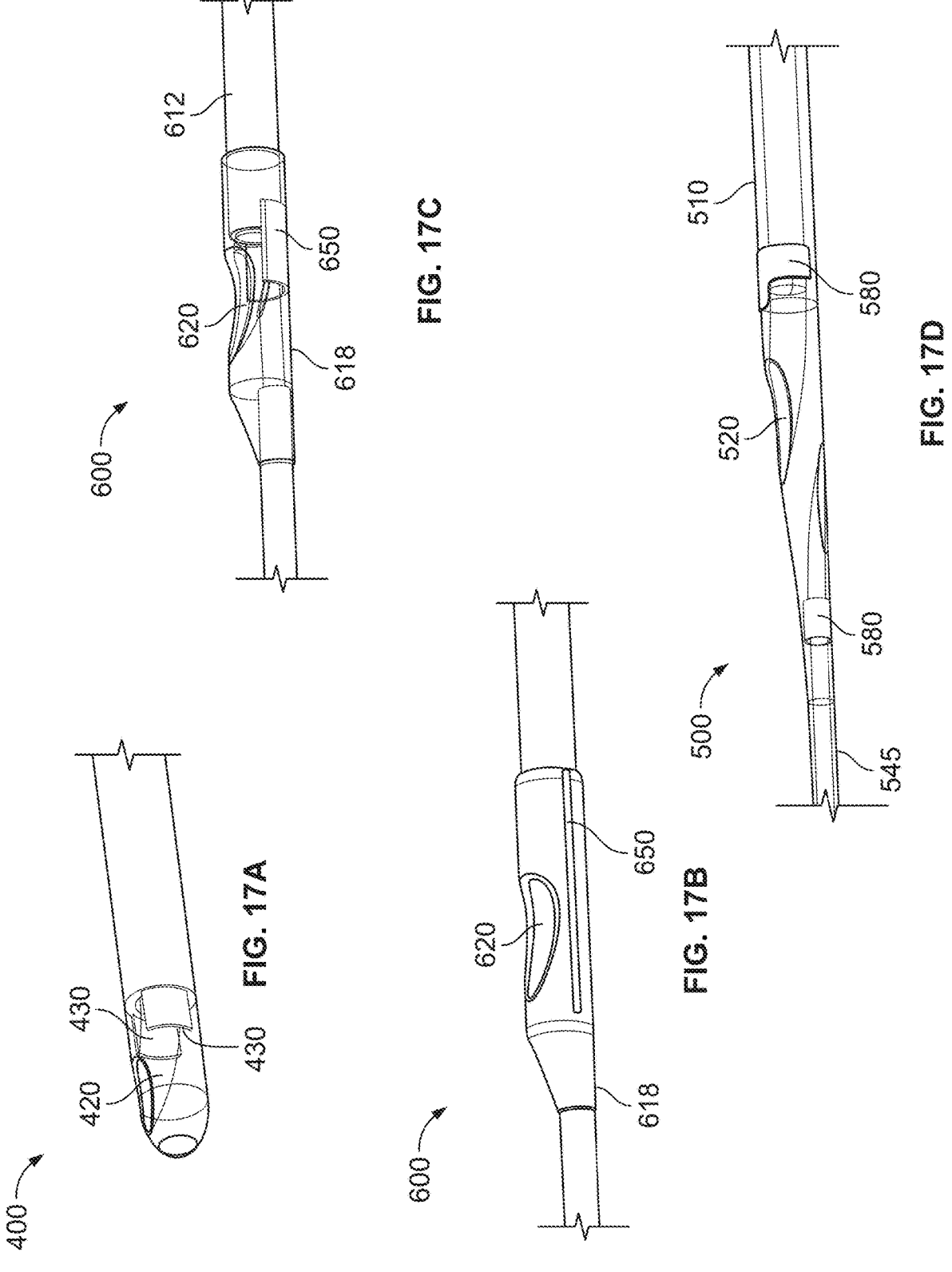
FIGS. 17A-17D illustrate various radiopaque markers in different configurations on different puncture system delivery systems, according to embodiments.

FIG. 17A illustrates the system 400 with two quarter-ring radiopaque markers 430 opposite each other outside of the lateral wall leading up to or over a portion of the puncture system exit port 420. Two quarter-ring radiopaque markers, such as ones that are opposite, may be beneficial because the gap between the two quarter-ring radiopaque markers could be used to determine whether the puncture system exit port 420 is pointing in the anterior or posterior direction when using an anterior-posterior fluoroscopic view. However, the two quarter-ring radiopaque markers 430 would not be able to differentiate specifically between the anterior direction and the posterior direction.

FIG. 17B illustrates the system 600 (also shown in FIG. 7B) with an elongated radiopaque marker 650 extending along an axial length of the connector 618. On the opposite side of the connector 618 (not visible) there may be a shorter elongated radiopaque marker 650 extending along an axial length of the connector 618. The elongated radiopaque markers 650 may be rod shaped or have a flat rectangular shape or other suitable shape. Such an arrangement can provide an orientation of the system 600, and particularly the puncture system exit port 620, in the AP and oblique views during fluoroscopic imaging.

FIG. 17C illustrates the system 600 (also shown in FIG. 7B) with a half-ring radiopaque marker 650 underneath a portion of the puncture system exit port 620 on the connector 618, and under a portion of the proximal catheter 612. Such half ring radiopaque markers can provide accurate positioning of the system 600, and particularly the puncture system exit port 620, in a lateral fluoroscopic view.

FIG. 17D illustrates the system 500 with an entirely circumferential radiopaque marker 580 on the distal catheter and a T-shaped half-ring radiopaque marker 580 on the proximal catheter 510. The "T" prong is shown as extending distally, but it could extend proximally as well. Such a T-shaped (e.g., half-ring) radiopaque marker 580 can indicate orientation of the system 500, and particularly the puncture system exit port 520 in the fluoroscopic AP, oblique, and lateral views.

Figure 18A:
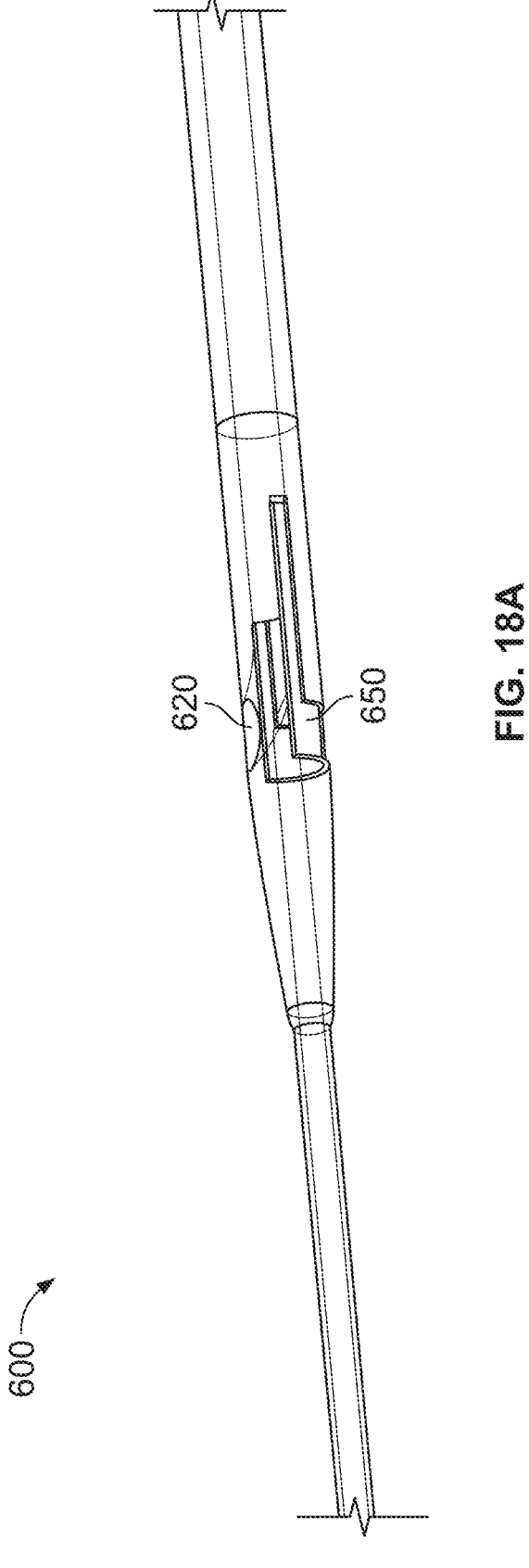
FIGS. 18A-18D illustrate different views of a radiopaque marker on a puncture system delivery system, according to embodiments.
Figures 18B, 18C, 18D:
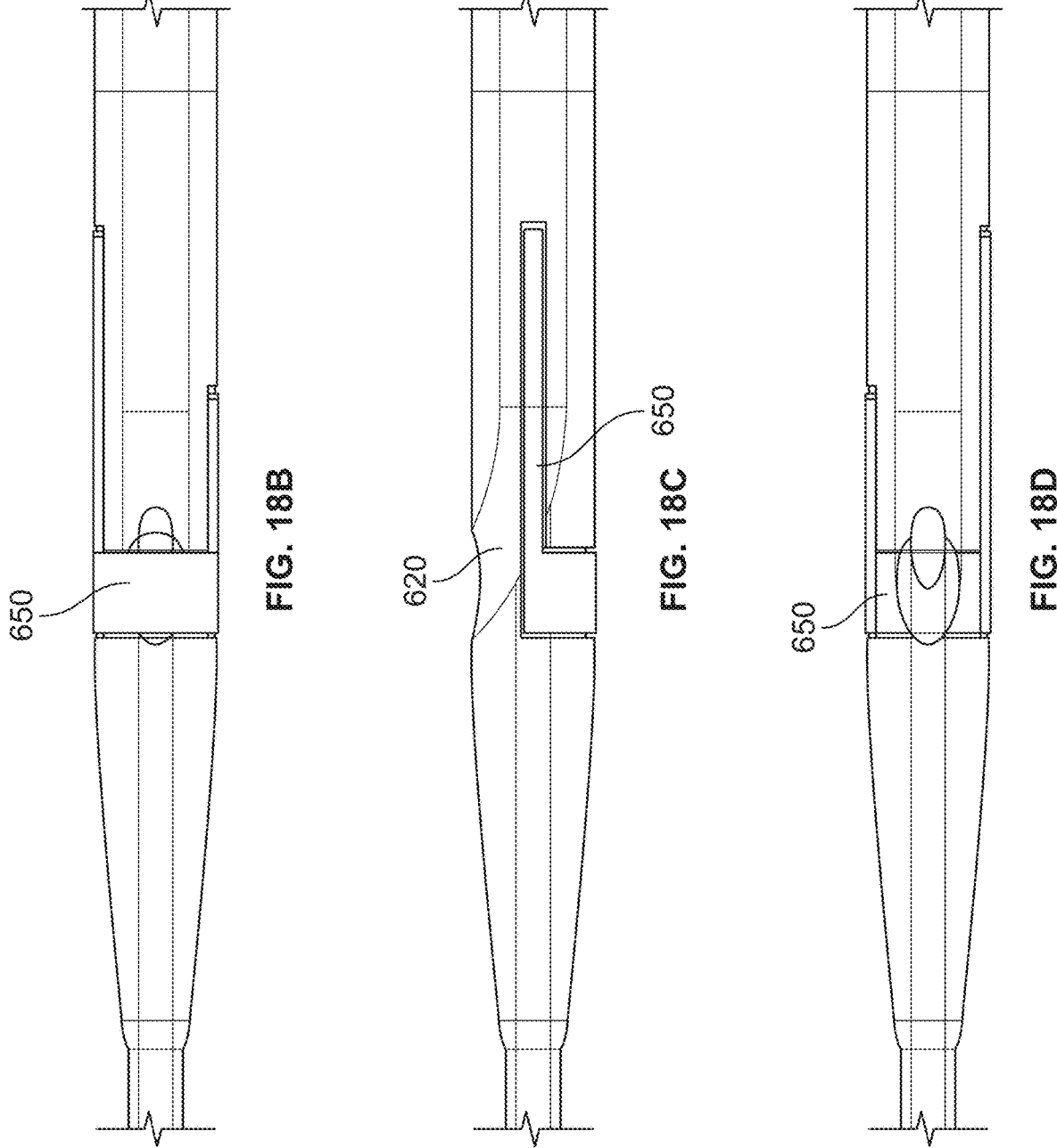

FIGS. 18A-18D illustrate another example of a radiopaque marker 650, in this example, in system 600 (also shown in FIG. 7A). Again, the radiopaque marker 650 can facilitate orientation to the surgeon during fluoroscopic viewing of the system 600, and particularly the puncture system exit port 620. All views in FIGS. 18A-18D show the system 600 in transparency with the radiopaque marker 650 opaque. FIG. 18A is a perspective view. FIG. 18B is a bottom view. FIG. 18C is a lateral view. FIG. 18D is a top view. The radiopaque marker 650 includes two, different length strips that are located approximately 180 degrees offset from one another, and 90 degrees offset from the puncture system exit port 620, although other orientations are possible. The strips extend along an axial dimension of the system 600 proximally, although they could extend distally. A 180-degree circumferential band (half-ring) connects the two strips, although other circumferential extents are possible. The circumferential band extends at least partially below the puncture system exit port 620. As with other radiopaque markers described herein, the radiopaque marker 650 could include a radiopaque metal, such as platinum/iridium or gold, or it could include a radiopaque loaded plastic such a BaSO4 loaded Pebax (e.g., 20% BaSO4 loaded Pebax). The radiopaque marker 650 could also be plated onto the system 600, e.g., using gold plating techniques.

FIG. 18B shows the radiopaque marker 650 as it would be seen from an AP view under fluoroscopy. The relative location of the long arm, the short arm, and the half-ring band may be used to determine the puncture system exit port 620 orientation under single plane fluoroscopy. In the example shown, the surgeon can rotate the system 600 until the two arms on the radiopaque marker 650 are at the maximal distance apart and the longer arm is cranial to the short arm to achieve posterior orientation. The positioning of the long and short arms could be inverted for when the system 600 is being used on the other side of the patient.

Figure 19:
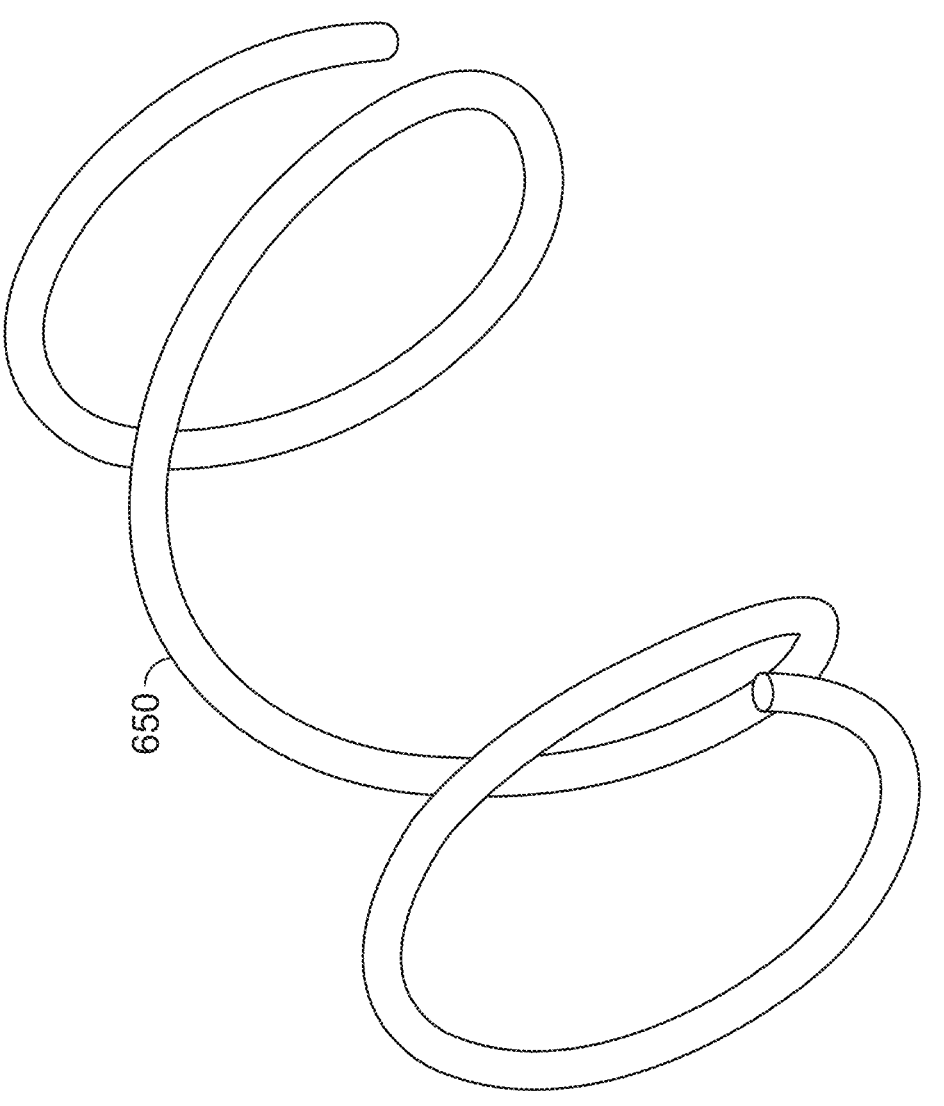
FIG. 19 illustrates a radiopaque marker, according to embodiments.
Figures 20A, 20B:
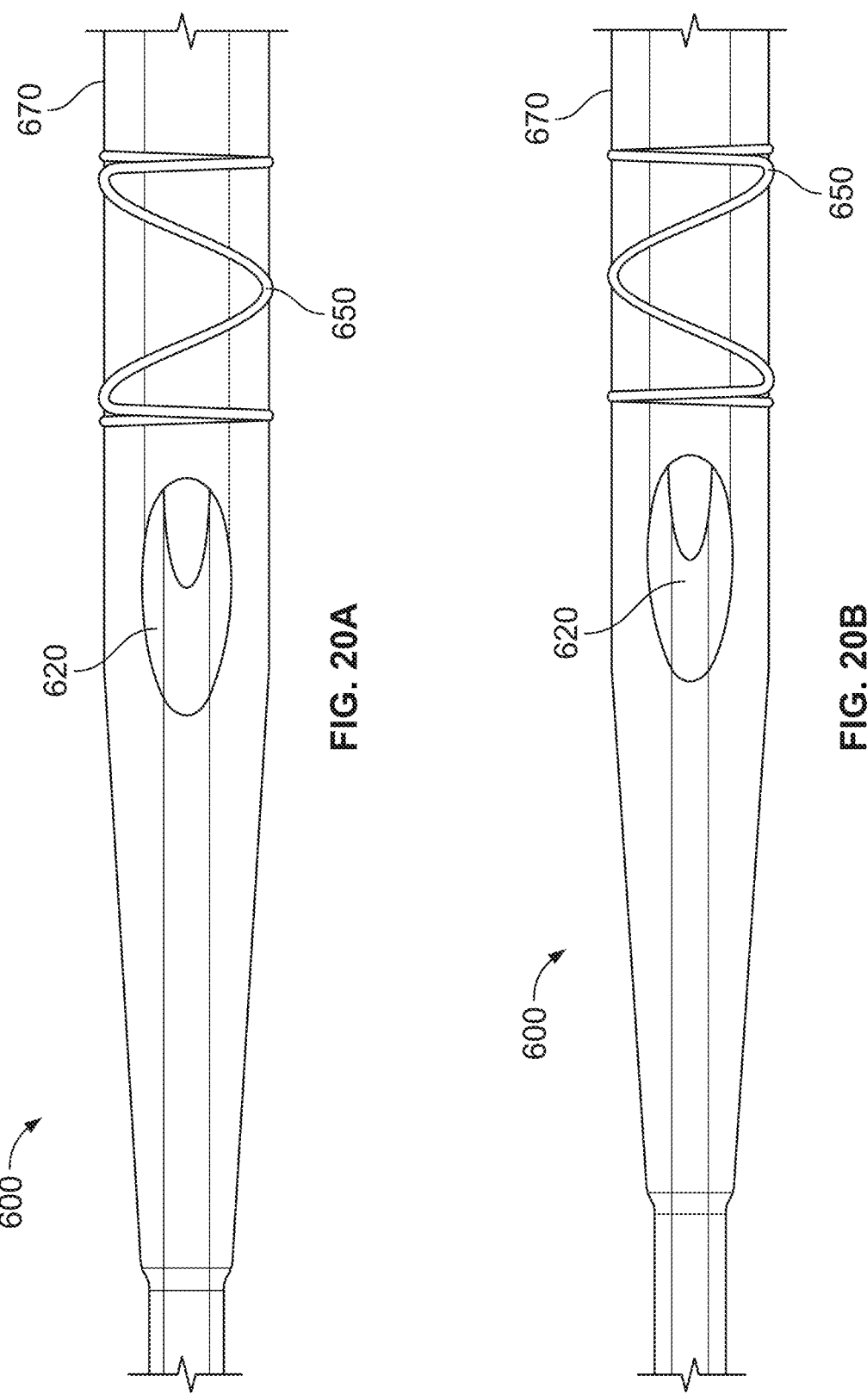
FIGS. 20A and 20B illustrate different views of a radiopaque marker on a puncture system delivery system, according to embodiments.

FIGS. 19, 20A, and 20B illustrate another example of a radiopaque marker 650 with system 600 (also shown in FIG. 7A). In this example, the radiopaque marker 650 includes a radiopaque wire, wrapped in a closed spring like pattern with a pitch coil (FIG. 19). The radiopaque marker 650 can be located on the proximal catheter 670, though it may also be located distally from the puncture system exit port 620. Depending on the rotational orientation of the radiopaque marker 650 relative to the puncture system exit port 620, the surgeon can determine the orientation of the puncture system exit port 620 under fluoroscopy. In the figure below, the orientation marker band looks like an "M" under AP view when the distal end of the system 600 is pointing to the left, and the puncture system exit port 620 is pointing posteriorly (FIG. 20A). The orientation marker band would look like a "W" if the distal end of the system 600 is pointing to the left and the puncture system exit port 620 is pointing anteriorly (FIG. 20B). Multiple wire radiopaque markers 650 may be used, such as one proximal and one distal the puncture system exit port 620.

Figures 21, 22:
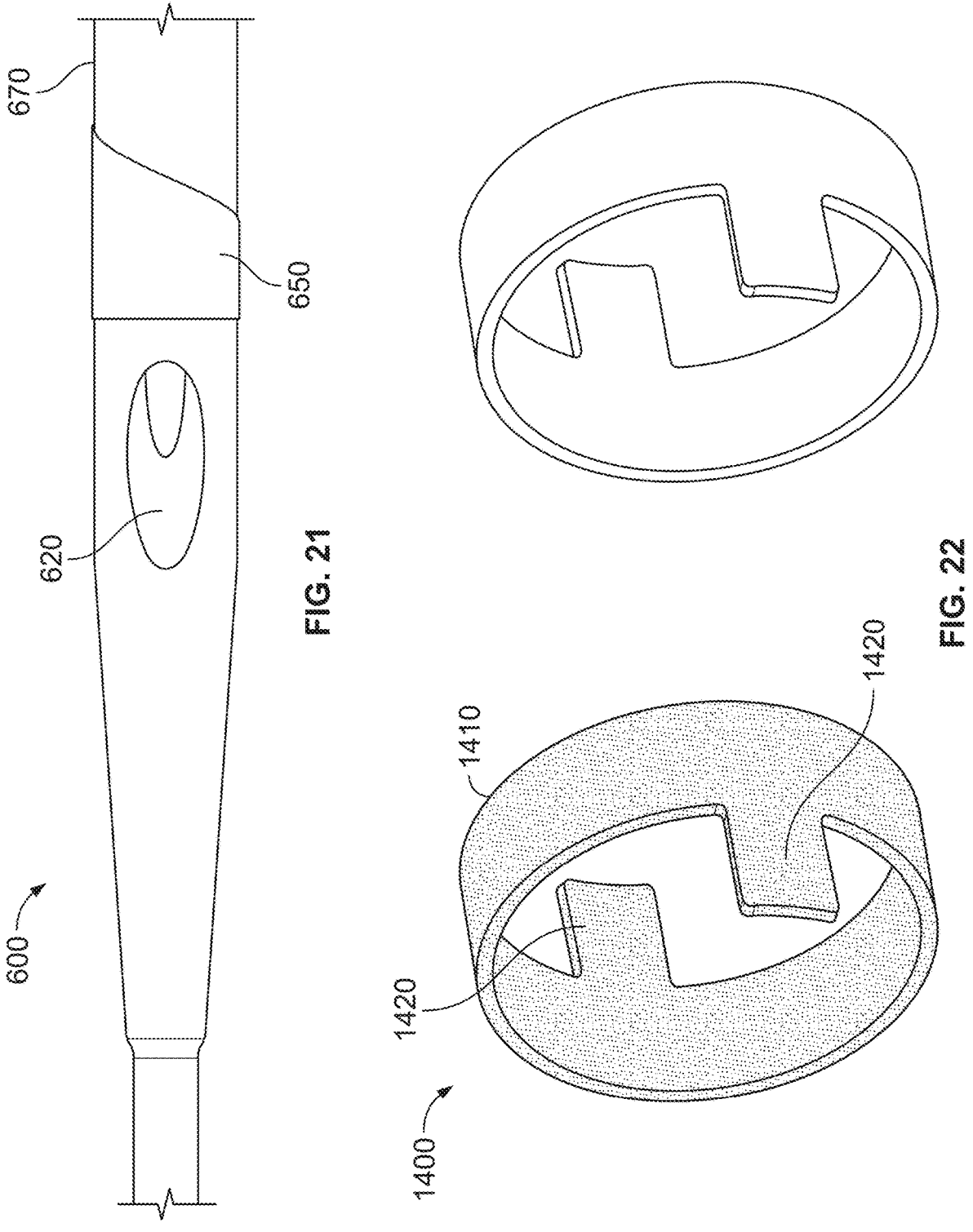
FIG. 21 illustrates a radiopaque marker on a puncture system delivery system, according to embodiments.
FIG. 22 illustrates a radiopaque marker, according to embodiments.

FIG. 21 illustrates another example of a radiopaque marker 650 with system 600 (also shown in FIG. 7A). In this example, the radiopaque marker 650 is shown as a circumferential ring (e.g., full ring) with the proximal end being contoured at an angle (although the distal end could alternatively/additionally be contoured at an angle). The surgeon may determine the puncture system exit port 620 orientation by the positioning of the "point" made by the angled contour(s). The radiopaque marker 650 is shown on the proximal catheter 670 but may be located distally from the puncture system exit port 620. Multiple radiopaque markers 650 may be used, such as one proximal and one distal the puncture system exit port 620.

FIG. 22 illustrates another exemplary radiopaque marker 1400, which has a chiral orientation. The radiopaque marker 1400 can be used to help determine orientation of a catheter (such as the various catheters described herein) and/or puncture system exit port with respect to one plane of fluoroscopy visualization. The radiopaque marker 1400 includes a band 1410 and strips 1420. The strips 1420 are shown as being equal length, extending in opposite directions (distally and proximally), and offset by 180 degrees.

Figures 23A, 23B, 23C:
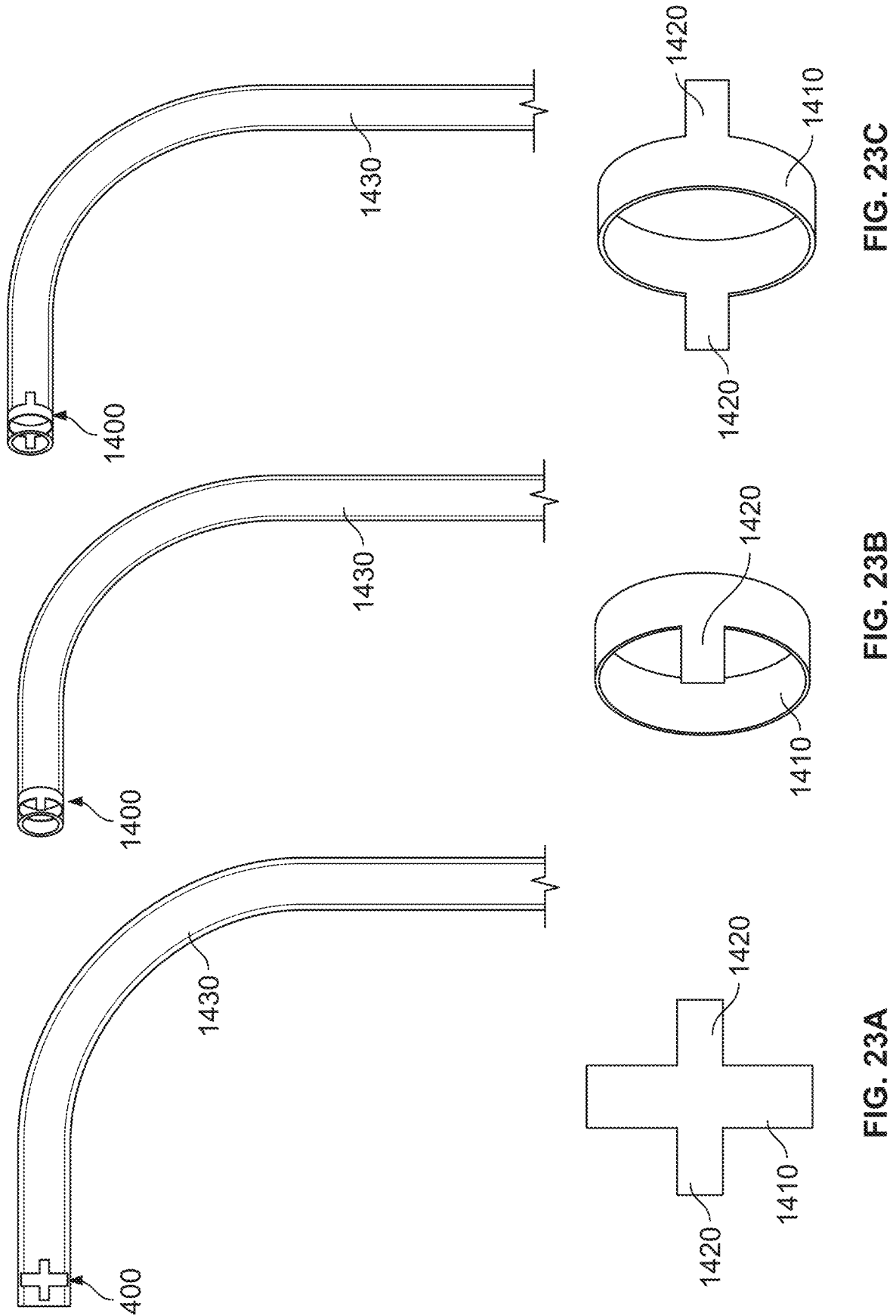
FIGS. 23A-23C illustrate a radiopaque marker on a catheter in different positions, according to embodiments.

FIGS. 23A-23C illustrates the radiopaque marker 1400 on a catheter 1430, wherein the assembly is in three different positions. The catheter 1430 is curved. A close-up view of the radiopaque marker 1400 is shown below the assembly above in each figure. The illustrations are in an AP fluoroscopy view. In FIG. 23A, the surgeon can understand that the catheter 1430 is in plane with the page because the strips 1420 point along the shaft of the catheter 1430, with the band 1410 forming a straight vertical line. In FIG. 23B, the surgeon can understand that the catheter 1430 is in a position where the tip of the catheter 1430 is pointing somewhat anteriorly (out of the page). In this example, the strips 1420 on the radiopaque marker 1400 are pointing towards each other, with a space within the band 1410 visible, showing the surgeon the catheter 1430 orientation. In FIG. 23C, the surgeon can understand that the catheter 1430 is in a position where the tip of the catheter 1430 is pointing somewhat posteriorly (into the page). The strips 1420 on the radiopaque marker 1400 are pointing outwards from each, with a space within the band 1410 visible, showing the surgeon the catheter 1430 orientation.

Figure 24B:
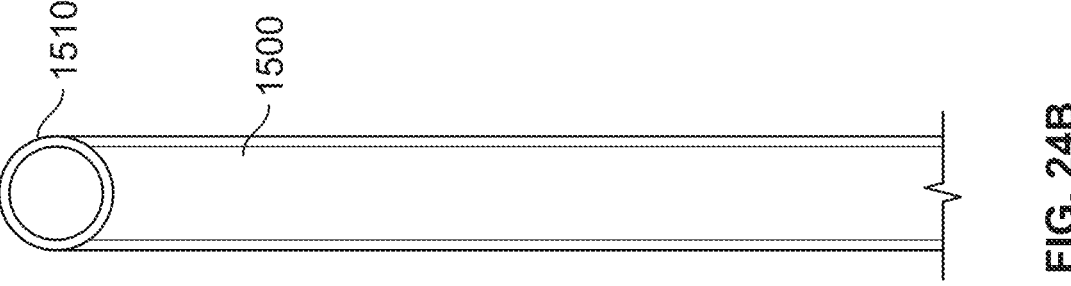
FIGS. 24A and 24B illustrate radiopaque markers on a catheter in different positions, according to embodiments.
Figure 24A:
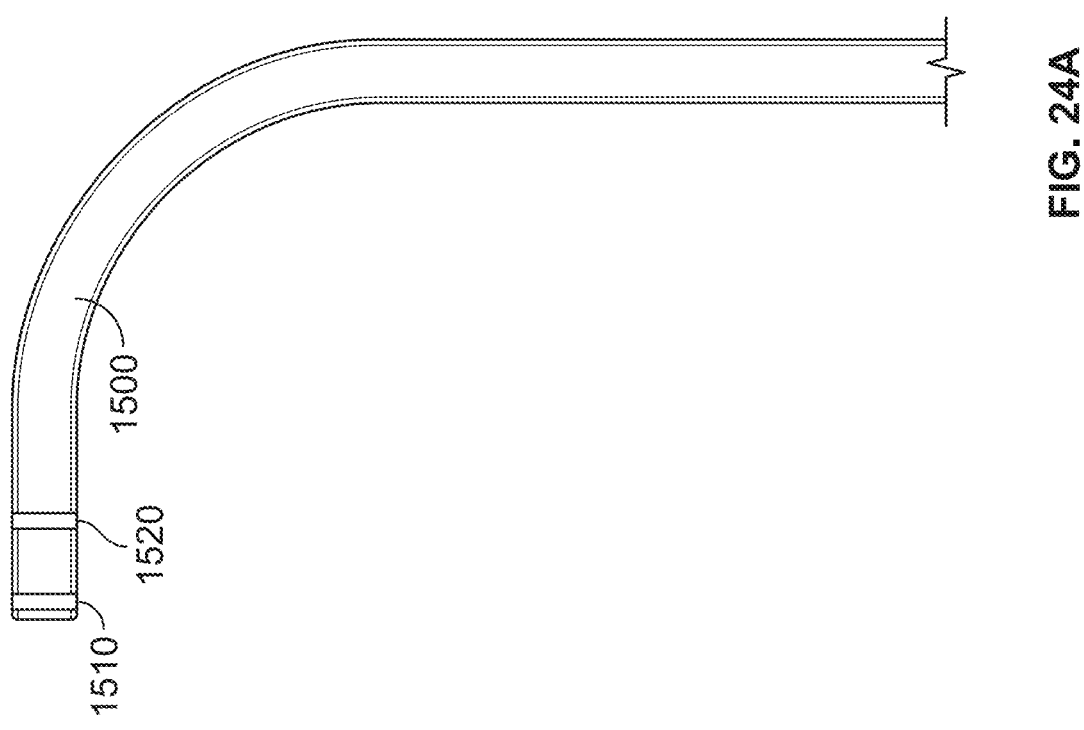

FIG. 24A-26B illustrate another exemplary radiopaque marker technique. As shown in FIG. 24A, two spaced radiopaque markers 1510, 1520 (in this example, circumferential bands) are located on a catheter 1500 (e.g., the

Figure 25B:
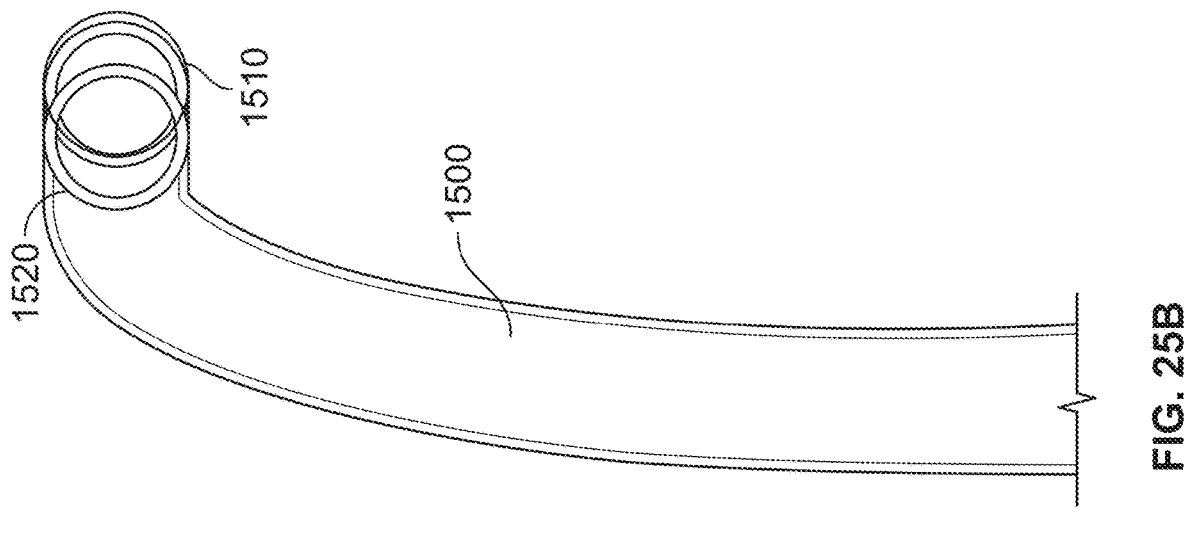
FIGS. 25A and 25B illustrate radiopaque markers on a catheter in different positions, according to embodiments.
Figure 25A:
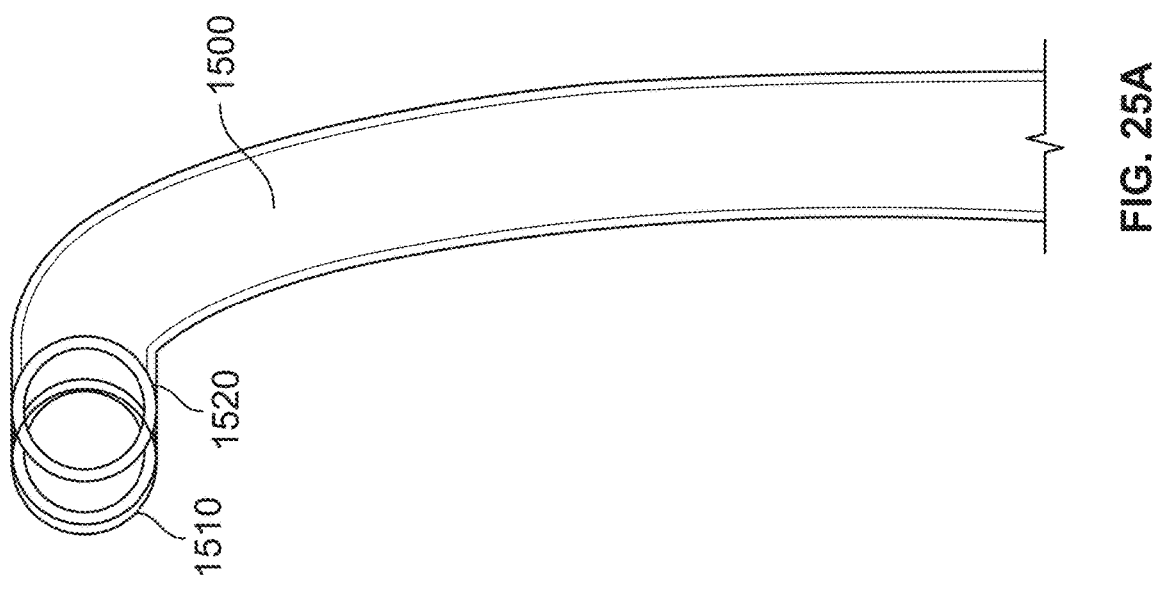
Figure 26B:
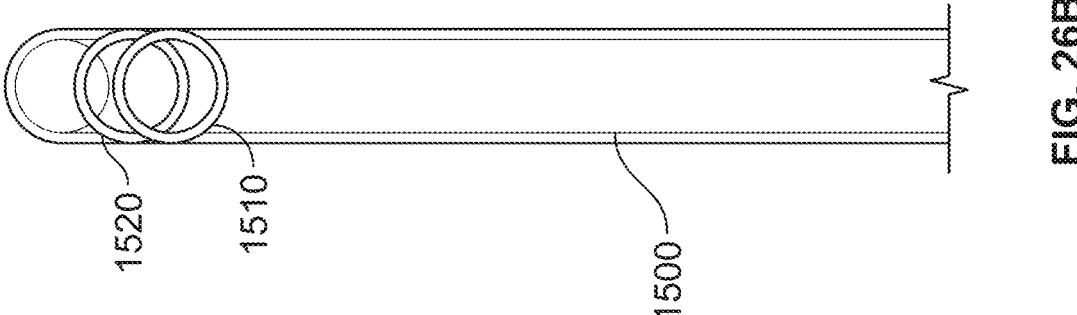
FIGS. 26A and 26B illustrate radiopaque markers on a catheter in different positions, according to embodiments.
Figure 26A:
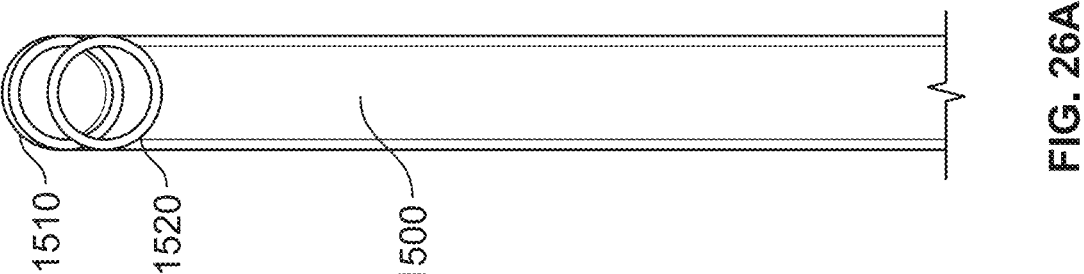

17 catheters described herein). These radiopaque markers 1510, 1520 can be used to determine proper orientation of the catheter 1500 (particularly the distal tip of the catheter 1500) in the lateral plane of fluoroscopy. The radiopaque markers 1510, 1520 are shown proximate the distal tip of the catheter 1500. The radiopaque markers 1510, 1520 can be separated by a known distance, such as 5 mm, though they could be separated by between 3 mm to 15 mm. Radiopaque marker 1510 can be positioned 0.5 mm from the distal tip of the catheter 1500, to provide the surgeon visualization of the catheter 1500 distal region. In this example below, the radiopaque markers 1510, 1520 are the same width (e.g., 1 mm), though they could be different widths or thickness to differentiate between the two under fluoroscopy. The widths could vary, for example, from 0.5 mm to 4 mm. FIG. 24A shows the catheter 1500 and radiopaque markers 1510, 1520 in the AP view. FIG. 24B shows the same assembly in the lateral fluoroscopy view. In this example, radiopaque marker 1510 overlaps radiopaque marker 1520 in this view, confirming to the surgeon that the tip of the catheter 1500 is perpendicular to the lateral view. FIG. 25A shows the tip of the catheter 1500 pointing somewhat anteriorly, with the radiopaque markers 1510, 1520 not in alignment. FIG. 25B shows the tip of the catheter 1500 pointing somewhat posteriorly, with the radiopaque markers 1510, 1520 not in alignment. FIG. 26A shows the tip of the catheter 1500 pointing somewhat superiorly, with the radiopaque markers 1510, 1520 not in alignment. FIG. 25B shows the tip of the catheter 1500 pointing somewhat inferiorly, with the radiopaque markers 1510, 1520 not in alignment.

Figures 27A, 27B:
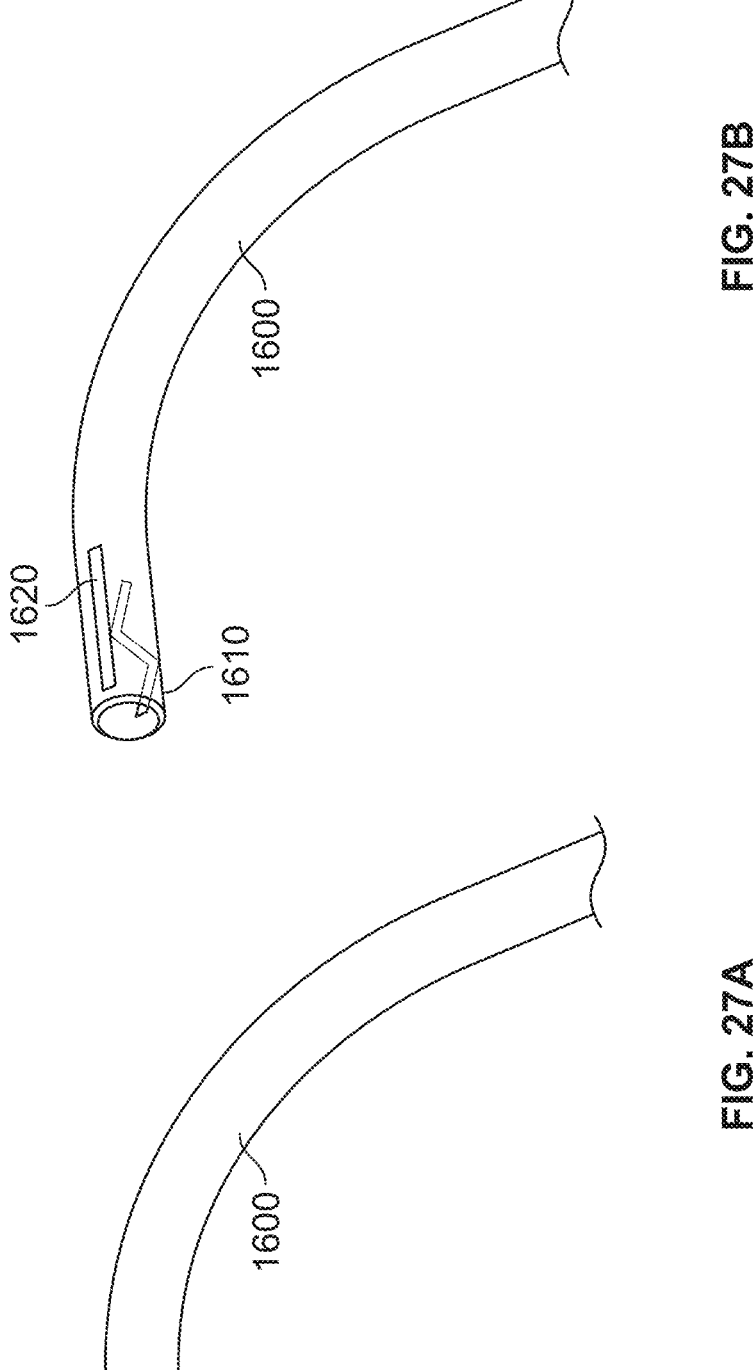
FIGS. 27A and 27B illustrate radiopaque markers on a catheter, according to embodiments.

FIG. 27A illustrates another example of radiopaque markers (in this example, markers 1610, 1620) used to provide information to a surgeon during fluoroscopy about the position of a portion of a catheter (in this example, catheter 1600) for example a puncture system exit port. The radiopaque markers 1610, 1620 (e.g., radiopaque wires) are elongated and run along the sides proximate to the distal tip of the catheter 1600. These radiopaque markers 1610, 1620 can provide information to the surgeon during fluoroscopy to confirm, in this example, catheter 1600 tip orientation with various fluoroscopy views. Radiopaque markers 1610, 1620 are positioned 180 degrees apart from each other in or on the wall of the catheter 1600. These wires are, for example, 6 mm in length, though they could be anywhere from, for example, 2 mm to 20 mm in length. The radiopaque markers 1610, 1620 in the example below are positioned 1 mm from the tip of the catheter 1600 to help visualize the region proximate the tip of the catheter 1600 under fluoroscopy. The radiopaque markers 1610, 1620 can be round or flat, and there could be any suitable number of markers along the wall of the catheter 1600. For example, there could be four wires, 90 degrees offset from each other in the wall of the catheter 1600. One or more of the markers could be a different length, to help differentiate between the wires under fluoroscopy.

As shown in FIG. 27B, radiopaque markers 1610, 1620 can have different shapes, such as one including a squiggle or zig-zag to provide differentiation information to the surgeon between the radiopaque markers 1610, 1620. The thickness of the radiopaque markers 1610, 1620 can also vary to provide differentiation information to the surgeon.

Figures 28A, 28B, 28C:
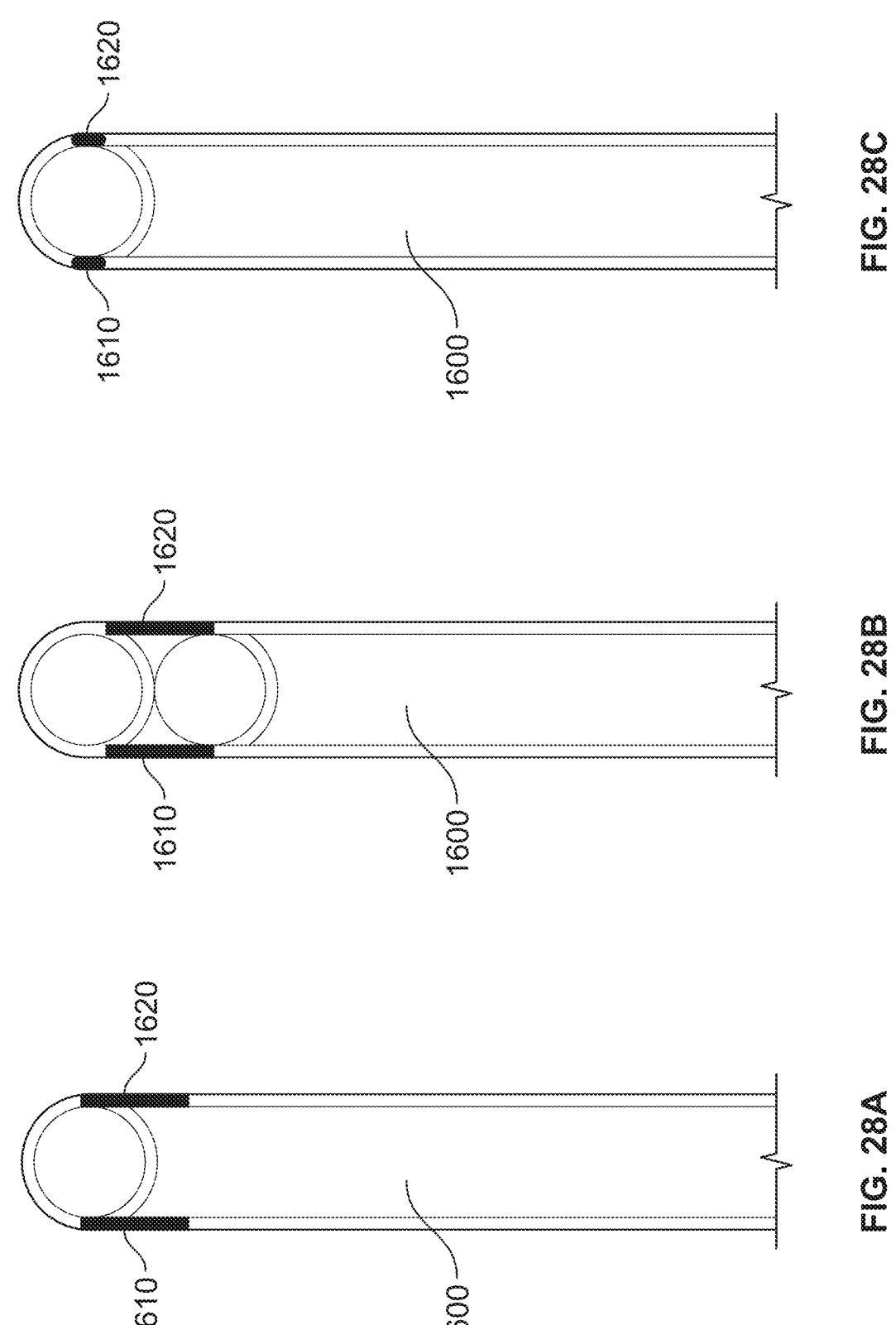
FIGS. 28A-28C illustrate radiopaque markers on a catheter in different positions, according to embodiments.

FIGS. 28A-28C shows radiopaque markers 1610, 1620 and catheter 1600 in various orientations in the lateral view. FIG. 28A and FIG. 28B show the catheter 1600 pointing somewhat inferiorly and somewhat superiorly, respectively. The surgeon can use the proportional length of the radiopaque markers 1610, 1620 in the lateral view to determine the orientation of the region proximal to the tip of the catheter 1600. FIG. 28C shows the catheter 1600 pointing perpendicularly to the lateral fluoroscopy view, as the radiopaque markers 1610, 1620 are presenting with their smallest length. In such a way, the surgeon can understand the orientation of a portion of the catheter 1600, such as the tip.

Figure 29:
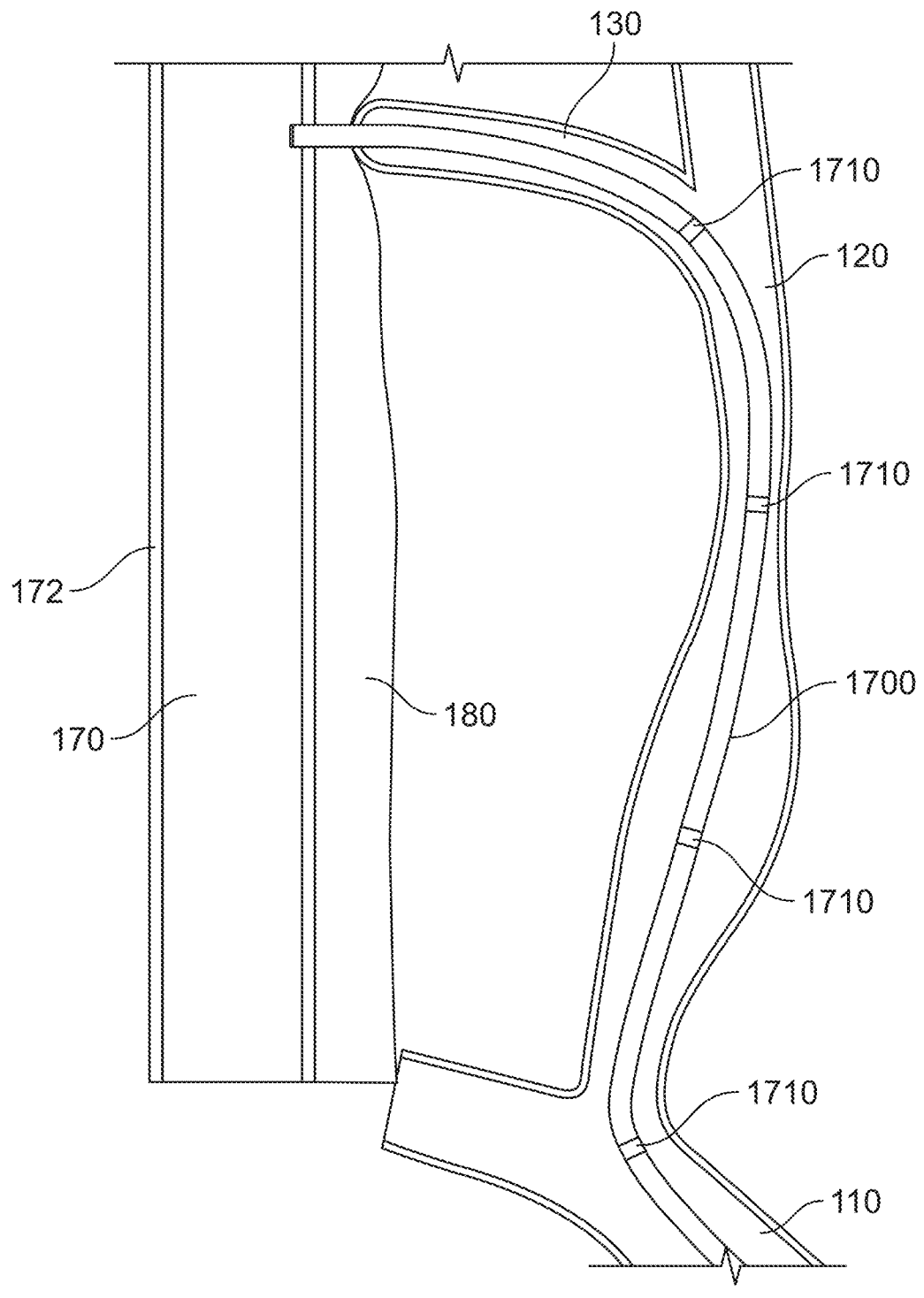
FIG. 29 illustrates radiopaque markers placed at predetermined locations along a catheter in a patient's anatomy, according to embodiments.

As shown in FIG. 29, radiopaque markers 1710 can be placed at predetermined locations along a catheter 1700 to help assist in length assessment for a CSF shunt. In this case, the catheter 1700 is to facilitate delivering a CSF shunt. It can be beneficial that a flow regulator on the CSF shunt be placed in a relatively large, straight portion of a vessel (e.g., an intervertebral vein, ascending lumbar vein, iliac vein, femoral vein or inferior vena cava as examples). The surgeon can choose a proper length CSF shunt or cut/alter a CSF shunt to be a specific length during the pre-delivery phase of the procedure using the specified locations of the marker bands on the catheter 1700 to ensure that a suitable CSF shunt length is chosen for the given patient's anatomy.

In the example, four radiopaque markers 1710 are on the shunt delivery system catheter 1700 at intervals corresponding to the various CSF shunt lengths the physician could implant. The distal tip of the shunt delivery system catheter 1700 is shown across the intervertebral vein 130 wall, interstitial tissue 180, and lumbar dura 172, and into the thecal sac 170 between the T3 and T4 vertebrae (vertebrae not shown). The distal most radiopaque marker 1710 is placed in this example at 4 cm from the distal tip of the catheter 1700, but it could be placed anywhere between, for example, 2 cm and 8 cm. In this example, the distal most radiopaque marker 1710 is located at the anastomosis between the ascending lumbar vein 120 and intervertebral vein 130. This may be a suitable shunt length for the patient because, in the example, a shunt flow regulator would exit the intervertebral vein 130 slightly and not be positioned against a vessel wall, thereby reducing the chance of flow regulator blockage. The next two proximal radiopaque markers 1710 in this example are positioned in the ascending lumbar vein 120, 8 cm and 12 cm from the distal tip of the catheter 1700, respectively. They could be placed at other locations, for example between 6 cm and 16 cm from the distal tip of the catheter 1700. The third radiopaque marker 1710 shows an example of a location in the ascending lumbar vein 120, which could be advantageous for positioning a flow regulator due to a lower likelihood of blocking the vessel or overgrowth around the flow regulator. Similarly, the fourth radiopaque marker 1710 (located at 16 cm from the distal tip of the catheter 1700 in this example) exits into the iliac vein 110, which could be a suitable location for the flow regulator to reside due to the large size of the iliac vein 110. This radiopaque marker 1710 could be placed, for example, between 14 cm and 25 cm from the distal tip of the catheter 1700. The locations of these radiopaque markers 1710 could vary based on shunt length or lumbar puncture location. There could also be more or fewer radiopaque markers 1710 for shunts of different lengths. The radiopaque markers 1710 may also be at regular intervals along the catheter 1700, for example, between 2 mm and 10 mm, independent of shunt lengths to serve as a measurement system for the surgeon.

Different arrangements of the components depicted in the drawings or described above, as well as components and steps not shown or described are possible. Similarly, some features and sub-combinations are useful and may be employed without reference to other features and sub-combinations. Embodiments of the present disclosure have been described for illustrative and not restrictive purposes, and alternative embodiments will become apparent to readers of this disclosure. In certain cases, method steps or operations may be performed or executed in differing order, or operations may be added, deleted or modified. It can be appreciated that, in certain aspects of the present disclosure, a single component may be replaced by multiple components, and multiple components may be replaced by a single component, to provide an element or structure or to perform a given function or functions.

It will be understood by those skilled in the art that various changes may be made and equivalents may be substituted without departing from the scope of the novel techniques disclosed in this application. In addition, many modifications may be made to adapt a particular situation or material to the teachings of the novel techniques without departing from its scope.

Parts List:

| Part No | Description |
| --- | --- |
| 100 | lumbar region |
| 110 | iliac vein(s) |
| 120 | ascending lumbar vein(s) |
| 130 | intervertebral vein(s) |
| 140 | epidural venous plexus |
| 150 | foramen |
| 160 | vertebral body |
| 170 | thecal sac |
| 172 | dura |
| 180 | Interstitial tissue |
| 190 | inferior vena cava |
| 300 | system |
| 310 | main catheter |
| 320 | pull ring |
| 330 | pull wire |
| 340 | pull wire tube |
| 350 | reinforcement |
| 360 | tip |
| 370 | inner catheter |
| 380 | radiopaque marker(s) |
| 390 | articulation zone |
| 392 | segment |
| 400 | system |
| 410 | catheter |
| 420 | puncture system exit port |
| 430 | quarter-ring radiopaque markers |
| 500 | system |
| 510 | proximal catheter |
| 520 | puncture system exit port |
| 530 | primary navigation guide wire port |
| 540 | distal lumen |
| 545 | distal catheter |
| 550 | puncture catheter lumen |
| 560 | primary navigation guidewire |
| 570 | puncture system |
| 580 | radiopaque markers |
| 590 | distal zone |
| 600 | system |
| 602 | guide catheter |
| 610 | proximal lumen |
| 612 | proximal catheter |
| 614 | distal catheter |
| 616 | distal passageway |
| 618 | connector |
| 620 | puncture system exit port |
| 622 | proximal recess |
| 624 | distal recess |
| 630 | puncture system |
| 631 | guidewire |
| 632 | catheter |
| 640 | primary navigation guidewire |
| 650 | radiopaque marker(s) |
| 660 | distal lumen |
| 670 | proximal catheter |

-continued

Parts List:

| Part No | Description |
| --- | --- |
| 680 | distal catheter |
| 700 | system |
| 710 | proximal shaft |
| 720 | distal shaft |
| 730 | puncture system exit port |
| 740 | puncture system lumen |
| 750 | guide wire lumen |
| 800 | needle |
| 810 | tip |
| 820 | body |
| 900 | stylet |
| 910 | tip |
| 920 | body |
| 1000 | needle |
| 1010 | tip |
| 1020 | body |
| 1100 | needle |
| 1110 | tip |
| 1120 | body |
| 1130 | hybridized stylet/guidewire |
| 1200 | stylet system |
| 1210 | stylet tip |
| 1220 | hollow shaft |
| 1230 | stylet body |
| 1300 | system |
| 1310 | aperture |
| 1320 | puncture system |
| 1400 | radiopaque marker |
| 1410 | band |
| 1420 | strips |
| 1430 | catheter |
| 1500 | catheter |
| 1510 | radiopaque marker |
| 1520 | radiopaque marker |
| 1600 | catheter |
| 1610 | radiopaque markers |
| 1620 | radiopaque markers |
| 1700 | catheter |
| 1710 | radiopaque markers |

The invention claimed is:

1. A system for delivering a puncture system to puncture through a wall of a patient's blood vessel, the system comprising:

a proximal catheter including a proximal lumen configured to accommodate both a primary navigation guide wire and the puncture system;

a puncture system exit port in communication with the proximal lumen, wherein the puncture system exit port is configured to receive the puncture system, such that a portion of the puncture system passes through the puncture system exit port and exits the system; and a distal catheter including a distal lumen in communication with the proximal lumen, wherein the distal lumen is configured to accept the primary navigation guide wire and reject the puncture system, such that the primary navigation guide wire is able to enter the distal lumen and the puncture system is not able to enter the distal lumen.

2. The system of claim 1, further comprising the puncture system, wherein the puncture system is configured to puncture through the wall of the blood vessel, interstitial tissue and dura mater into a thecal sac of the patient.

3. The system of claim 1, wherein the puncture system exit port is angled with respect to the center axis of the proximal lumen.

4. The system of claim 1, wherein a diameter of the proximal lumen is greater than a diameter of the distal lumen.

5. The system of claim 4, wherein a diameter of the puncture system exit port is greater than a diameter of the distal lumen.

6. The system of claim 1, wherein a diameter of the puncture system exit port is the same as a diameter of the proximal lumen where the puncture system exit port and the proximal lumen meet.

7. The system of claim 1, further comprising the puncture system, wherein the puncture system includes a stylet.

8. The system of claim 7, wherein the stylet is a bi-plane stylet.

9. The system of claim 7, wherein the stylet comprises Nitinol.

10. The system of claim 7, wherein the puncture system includes a catheter configured to pass over the stylet.

11. The system of claim 1, wherein the system further comprises:

a radiopaque marker on the proximal catheter; and a radiopaque marker on the distal catheter.

12. The system of claim 1, further comprising a connector connecting the proximal catheter and the distal catheter, wherein the puncture system exit port is in the connector.

13. The system of claim 1, further comprising at least one radiopaque marker configured to provide orientation information of the puncture system exit port during fluoroscopy.

14. The system of claim 13, further comprising the puncture system, wherein the puncture system is configured to puncture through the wall of the blood vessel, interstitial tissue and dura mater into a thecal sac of the patient.

15. The system of claim 13, further comprising a connector connecting the proximal catheter and the distal catheter, wherein the puncture system exit port is in the connector.

16. The system of claim 15, wherein the at least one radiopaque marker is located on the connector.

17. The system of claim 13, wherein the at least one radiopaque marker includes plurality of strips extending along an axial dimension of the system connected by a circumferential band.

18. The system of claim 17, wherein the plurality of strips is two strips, and wherein a first strip is longer than a second strip.

19. The system of claim 17, wherein the circumferential band of the radiopaque marker extends at least partially below the puncture system exit port.

* * * * *